United States Patent
Wichterle et al.

(10) Patent No.: US 9,733,237 B2
(45) Date of Patent: Aug. 15, 2017

(54) METHODS FOR IDENTIFYING CANDIDATES FOR THE TREATMENT OF NEURODEGENERATIVE DISEASES

(71) Applicants: Hynek Wichterle, New York, NY (US); Christopher E Henderson, New York (JP); Sebastian Thams, New York, NY (US)

(72) Inventors: Hynek Wichterle, New York, NY (US); Christopher E Henderson, New York (JP); Sebastian Thams, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/439,620

(22) PCT Filed: Oct. 31, 2013

(86) PCT No.: PCT/US2013/067819
§ 371 (c)(1),
(2) Date: Apr. 29, 2015

(87) PCT Pub. No.: WO2014/071042
PCT Pub. Date: May 8, 2014

(65) Prior Publication Data
US 2015/0285788 A1    Oct. 8, 2015

Related U.S. Application Data

(63) Continuation of application No. 61/721,013, filed on Oct. 31, 2012.

(51) Int. Cl.
| | |
|---|---|
| *C12N 5/07* | (2010.01) |
| *G01N 33/50* | (2006.01) |
| *A61K 31/404* | (2006.01) |
| *A61K 31/407* | (2006.01) |
| *A61K 31/519* | (2006.01) |

(52) U.S. Cl.
CPC ....... *G01N 33/5058* (2013.01); *A61K 31/404* (2013.01); *A61K 31/407* (2013.01); *A61K 31/519* (2013.01); *G01N 33/5014* (2013.01); *G01N 2333/914* (2013.01); *G01N 2500/00* (2013.01); *G01N 2500/10* (2013.01); *G01N 2800/28* (2013.01); *G01N 2800/2835* (2013.01)

(58) Field of Classification Search
None
See application file for complete search history.

(56) References Cited

U.S. PATENT DOCUMENTS

| | | |
|---|---|---|
| 2005/0014680 A1 | 1/2005 | Crabtree |
| 2007/0037882 A1 | 2/2007 | Kita et al. |
| 2010/0028931 A1 | 2/2010 | Eggan |
| 2012/0010178 A1 | 1/2012 | Rubin et al. |

OTHER PUBLICATIONS

DiBernardo et al., Translating preclinical insights into effective human trials in ALS, 2006, Biochimica et Biophysica Acta 1762:1139-1149.*
Alvarez, J. L., et al., 2010. Ahnakl modulates L-type Ca(2+) channel inactivation of rodent cardiomyocytes. Pflugers Arch 460, 719-730.
Batulan, Z., et al., 2006. Induction of multiple heat shock proteins and neuroprotection in a primary culture model of familial amyotrophic lateral sclerosis. Neurobiol Dis 24, 213-225.
Beltran-Parrazal, L., et al., 2012. Inhibition of endoplasmic reticulum Ca(2+) ATPase in preBotzinger complex of neonatal rat does not affect respiratory rhythm generation. Neuroscience 224C, 116-124.
Bevers, M. B., Neumar, R. W., 2008. Mechanistic role of calpains in postischemic neurodegeneration. J Cereb Blood Flow Metab 28, 655-673.
Blauw, H. M., et al., 2010. A large genome scan for rare CNVs in amyotrophic lateral sclerosis. Hum Mol Genet 19, 4091-4099.
Bosco, D. A., et al., 2010. Wild-type and mutant SOD1 share an aberrant conformation and a common pathogenic pathway in ALS. Nat Neurosci 13, 1396-1403.
Boulting, G. L., et al., 2011. A functionally characterized test set of human induced pluripotent stem cells. Nat Biotechnol 29, 279-286.
Brotherton, T. E., et al., 2012. Cellular toxicity of mutant SOD1 protein is linked to an easily soluble, nonaggregated form in vitro. Neurobiol Dis 49C, 49-56.
Carlson, S. S., et al., 2010. Presynaptic calcium channels and alpha3-integrins are complexed with synaptic cleft laminins, cytoskeletal elements and active zone components. J Neurochem 115, 654-666.
Chio, A., et al., 2009. A two-stage genome-wide association study of sporadic amyotrophic lateral sclerosis. Hum Mol Genet 18, 1524-1532.
Cleveland, D. W., Rothstein, J. D., 2001. From Charcot to Lou Gehrig: deciphering selective motor neuron death in ALS. Nat Rev Neurosci 2, 806-819.
Damiano, M., et al., 2006. Neural mitochondrial Ca2+ capacity impairment precedes the onset of motor symptoms in G93A Cu/Zn-superoxide dismutase mutant mice. J Neurochem 96, 1349-1361.
De Morree, A., et al., 2011. Self-regulated alternative splicing at the AHNAK locus. FASEB J. Jan;26(1):93-103.

(Continued)

*Primary Examiner* — John Ulm
(74) *Attorney, Agent, or Firm* — Bryan Cave LLP

(57) ABSTRACT

The present invention provides, inter alia, methods for identifying a candidate agent that may be effective to treat or ameliorate an effect of a neurodegenerative disease in a subject. These methods include: (a) contacting a wildtype neuron and a mutant neuron with a stressor which is effective to accelerate the degeneration of the mutant neuron; (b) further contacting the wildtype neuron and the mutant neuron from step (a) with a candidate agent; and (c) determining whether the candidate agent lowers a wildtype to mutant survival ratio or increases both wildtype and mutant neuron survival.

12 Claims, 20 Drawing Sheets

(56) References Cited

OTHER PUBLICATIONS

Dimos, J. T., et al., 2008. Induced pluripotent stem cells generated from patients with ALS can be differentiated into motor neurons. Science 321, 1218-1221.

Elden, A. C., et al., 2010. Ataxin-2 intermediate-length polyglutamine expansions are associated with increased risk for ALS. Nature 466, 1069-1075.

Foust, K. D., et al., 2009. Intravascular AAV9 preferentially targets neonatal neurons and adult astrocytes. Nat Biotechnol 27, 59-65.

Gehman, L. T., et al., 2011. The splicing regulator Rbfoxl (A2BP1) controls neuronal excitation in the mammalian brain. Nat Genet 43, 706-711.

Gemes, G., et al., 2011. Store-operated Ca2+ entry in sensory neurons: functional role and the effect of painful nerve injury. J Neurosci 31, 3536-3549.

Ghosh, B., et al., 2011. Inhibition of the plasma membrane Ca2+ pump by CD44 receptor activation of tyrosine kinases increases the action potential afterhyperpolarization in sensory neurons. J Neurosci 31, 2361-2370.

Goonasekera, S. A., et al., 2011. Mitigation of muscular dystrophy in mice by SERCA overexpression in skeletal muscle. J Clin Invest 121, 1044-1052.

Grosskreutz, J., et al., 2010. Calcium dysregulation in amyotrophic lateral sclerosis. Cell Calcium 47, 165-174.

Gruszczynska-Biegala, J., et al., 2011. Differential roles for STIM1 and STIM2 in store-operated calcium entry in rat neurons. PLoS One Apr. 26;6(4):e19285.

Igoudjil, A., et al., 2011. In vivo pathogenic role of mutant SOD1 localized in the mitochondrial intermembrane space. J Neurosci 31, 15826-15837.

International Search Report, mailed Jan. 29, 2014, for PCT/US2013/067819.

Jessup, M., et al., 2011. Calcium Upregulation by Percutaneous Administration of Gene Therapy in Cardiac Disease (CUPID): a phase 2 trial of intracoronary gene therapy of sarcoplasmic reticulum Ca2+-ATPase in patients with advanced heart failure. Circulation 124, 304-313.

Langou, K., et al., 2010. AAV-mediated expression of wild-type and ALS-linked mutant VAPB selectively triggers death of motoneurons through a Ca2+-dependent ER-associated pathway. J Neurochem 114, 795-809.

Lobsiger, C. S., et al., 2007. Toxicity from different SOD1 mutants dysregulates the complement system and the neuronal regenerative response in ALS motor neurons. Proc Natl Acad Sci USA 104, 7319-7326.

Mead, R. J., et al., 2011. Optimised and rapid pre-clinical screening in the SOD1(G93A) transgenic mouse model of amyotrophic lateral sclerosis (ALS). PLoS One 6, e23244.

Nadin, B. M., Pfaffinger, P. J., 2010. Dipeptidyl peptidase-like protein 6 is required for normal electrophysiological properties of cerebellar granule cells. J Neurosci 30, 8551-8565.

Nakagawa, T., Yuan, J., 2000. Cross-talk between two cysteine protease families. Activation of caspase-12 by calpain in apoptosis. J Cell Biol 150, 887-894.

Nakagawa, T., et al., 2000. Caspase-12 mediates endoplasmic-reticulum-specific apoptosis and cytotoxicity by amyloid-beta. Nature 403, 98-103.

Perrin, F. E., et al., 2006. Cell death pathways differ in several mouse models with motoneurone disease: analysis of pure motoneurone populations at a presymptomatic age. J Neurochem 98, 1959-1972.

Quinlan, K. A., et al., 2011. Altered postnatal maturation of electrical properties in spinal motoneurons in a mouse model of amyotrophic lateral sclerosis. J Physiol 589, 2245-2260.

Rabin, S. J., et al., 2010. Sporadic ALS has compartment-specific aberrant exon splicing and altered cell-matrix adhesion biology. Hum Mol Genet 19, 313-328.

Raoul, C., et al., 2002. Motoneuron death triggered by a specific pathway downstream of Fas. potentiation by ALS-linked SOD1 mutations. Neuron 35, 1067-1083.

Saxena, S., et al., 2009. A role for motoneuron subtype-selective ER stress in disease manifestations of FALS mice. Nat Neurosci 12, 627-636.

Saxena, S., Caroni, P., 2011. Selective neuronal vulnerability in neurodegenerative diseases: from stressor thresholds to degeneration. Neuron 71, 35-48.

Staats, K. A., et al., 2012. Dantrolene is neuroprotective in vitro, but does not affect survival in SOD1(G93A) mice. Neuroscience 220, 26-31.

Sun, W., et al., 2011. DPP6 establishes the A-type K(+) current gradient critical for the regulation of dendritic excitability in CA1 hippocampal neurons. Neuron 71, 1102-1115.

Towne, C., Aebischer, P., 2009. Lentiviral and adeno-associated vector-based therapy for motor neuron disease through RNAi. Methods Mol Biol 555, 87-108.

Tradewell, M. L., et al., 2011. Calcium dysregulation, mitochondrial pathology and protein aggregation in a culture model of amyotrophic lateral sclerosis: mechanistic relationship and differential sensitivity to intervention. Neurobiol Dis 42, 265-275.

Turner, B. J., Talbot, K., 2008. Transgenics, toxicity and therapeutics in rodent models of mutant SOD1-mediated familial ALS. Prog Neurobiol 85, 94-134.

Valdez, G., et al., 2012. Shared resistance to aging and ALS in neuromuscular junctions of specific muscles. PLoS One 7, e34640.

Van Den Bosch, L., et al., 1999. Calcium handling proteins in isolated spinal motoneurons. Life Sci 65, 1597-1606.

Wang, J., et al., 2009. Progressive aggregation despite chaperone associations of a mutant SOD1-YFP in transgenic mice that develop ALS. Proc Natl Acad Sci USA 106, 1392-1397.

Written Opinion of the International Searching Authority, mailed Jan. 29, 2014, for PCT/US2013/067819.

Yu, Q., Stamenkovic, I., 1999. Localization of matrix metalloproteinase 9 to the cell surface provides a mechanism for CD44-mediated tumor invasion. Genes Dev 13, 35-48.

Dimos et al., "Induced Pluripotent Stem Cells Generated from Patients with ALS Can Be Differentiated into Motor Neurons," Science, vol. 321, No. 5893, pp. 1218-1221 (Aug. 29,2008).

* cited by examiner

Figure 1
A
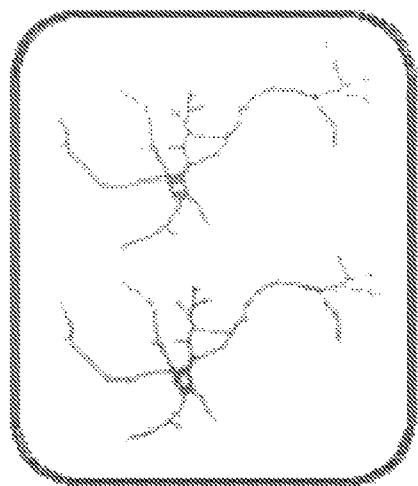 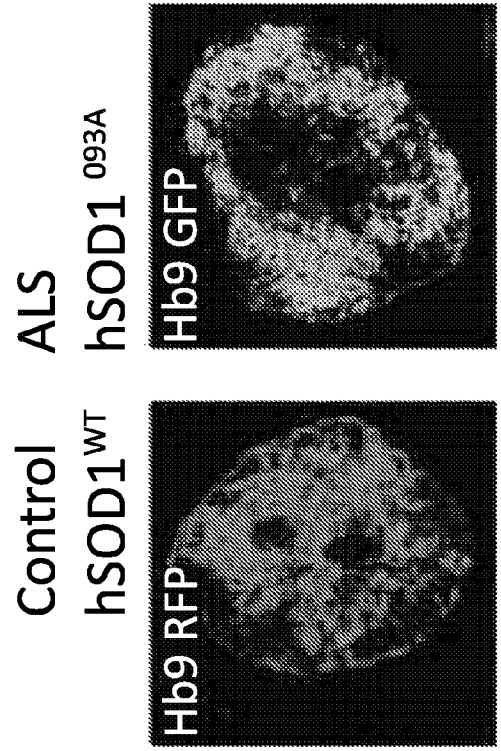
Control  ALS
hSOD1^WT  hSOD1^093A

Active rescue screen compounds

B

| Compound | Mechanism |
|---|---|
| Dorsomorphin | AMP-Kinase- and BMP inhibitor |
| Kenpaullone | CDK1/cyclin B, GSK-3β, HGK inhibitor (also inhibitor of CDK2/cyclin A, CDK2/cyclin E, CDK5/cyclin/p35) |
| PD 407824 | Inhibitor of check point kinases Chk1 and Wee1 (also ///, CDK4, PDGFR, FGFR) |
| Ro 31-8220 mesylate | PKC inhibitor (also inhibits GSK-3β, MAPKAP-K1b, MSK1, S6K1. Activates JNK and glycogen synthase, inhibits MAPK and ERK2). Inhibits voltage gated Na$^+$ channels. |
| Tauroursodeoxycholic acid (TUDCA) | Bile acid component, chemical chaperone, anti-apoptotic effect | ents
METHODS FOR IDENTIFYING CANDIDATES FOR THE TREATMENT OF NEURODEGENERATIVE DISEASES

CROSS-REFERENCE TO RELATED APPLICATIONS

The present application is the National Stage of International Application No. PCT/US2013/067819, which claims benefit to U.S. provisional application Ser. No. 61/721,013 filed Oct. 31, 2012, the entire contents of which above applications are incorporated by reference as if recited in full herein.

GOVERNMENT FUNDING

This invention was made with government support under grant numbers 1RC2NS069395 and 1U24NS078736-01 awarded by the National Institutes of Health. The government has certain rights in the invention.

FIELD OF INVENTION

The present invention provides, inter alia, screens/methods for identifying a candidate agent that may be effective to treat or ameliorate an effect of a neurodegenerative disease in a subject. Kits, pharmaceutical compositions and methods of treating or ameliorating the effects of a neurodegenerative disease with agents identified in such screens are also provided.

BACKGROUND OF THE INVENTION

Amyotrophic lateral sclerosis (ALS, also known as Lou Gehrig's disease) is a fatal neurological disease. In patients with ALS, degeneration and death of cortical and spinal motor neurons leads to progressive muscle paralysis, often starting in the distal limbs and progressing to the respiratory muscles (Cleveland and Rothstein, 2001). The number of new ALS cases per year worldwide is about 125,000. However, the sole approved drug, riluzole, confers only minor benefit. There is still no effective therapy for the adult-onset neurodegenerative disease ALS (amyotrophic lateral sclerosis). One major explanation is that very few therapeutic targets have been validated.

Therapeutic targets in ALS are rare. One of the major obstacles to a successful therapy for ALS is the near-absence of validated targets, molecular events in the disease pathway whose inhibition slows onset or progression. Genes such as superoxide dismutase 1 (SOD1) whose mutation can lead to ALS may be considered to be validated targets, but familial forms of the disease collectively represent only 10% of all cases. Therapeutic targets applicable to the 90% of sporadic cases would likely be key downstream effectors of the disease pathway, but no such intermediates have been validated. If genes acting early in the pathway can be identified, they will provide a solid foundation for targeted drug discovery programs.

Target discovery in mouse and human models of ALS. A great majority of studies on the mechanisms of ALS have focused on mouse models expressing disease-triggering mutant forms of SOD1 (Turner and Talbot, 2008). These mice develop a disease that is in many respects a close reflection of not only familial but also sporadic ALS, including selective resistance of oculomotor and slow spinal motor neurons (Valdez et al., 2012). However, even in this model, there are few validated targets other than the SOD1 gene itself. Moreover, concerns have been raised that results obtained in mSOD1 mice may not translate well to the clinic. Although this may in part reflect underpowered mouse preclinical studies, there is a need for human models to discover and validate novel candidate disease modifiers.

Although the disease mechanism involves other cell types, motor neuron dysfunction and degeneration are the defining features of the clinical phenotype, and cell-autonomous deficits in motor neurons are known to contribute to disease onset. It remains to be determined, however, how ALS motor neurons differ from their counterparts in healthy individuals at early stages of the disease, and this has hindered the development of assays for disease-modifying drugs. Strikingly, none of the many drugs that have undergone clinical trials in ALS was ever tested on the cells affected in the disease: sick human motor neurons. A reasonable strategy would be to evaluate candidate treatments in two systems in parallel: human motor neurons in vitro and the mouse neuromuscular system in vivo.

For this reason, the inventors have sought to use human induced pluripotent stem cells (hiPSCs) to model ALS in the culture dish. Multiple iPS lines from ALS patients and controls have been successfully generated and shown that they can be robustly differentiated in culture into motor neurons (iPS-MNs) and other spinal cord cell types such as astrocytes (Boulting et al., 2011; Dimos et al., 2008). However, to date, no spontaneous ALS-related phenotype has been reported in such cultures, perhaps because ALS is an adult-onset disease. Therefore, there is a need to better understand the molecular and functional differences between ALS and control iPS-MNs and to use this knowledge to identify disease-relevant neuroprotective agents.

Contribution of motor neuron hyperexcitability and $Ca^{++}$ imbalance to the ALS phenotype. Neuronal excitability reflects the critical balance of activation among dozens of membrane channels and their binding partners. Changes in the activation or inactivation properties of even a single channel can dramatically alter excitability of a single neuron or network of neurons. Any increase in membrane excitability ultimately results in elevations in intracellular $Ca^{++}$ concentration which, when excessively sustained, can result in cell death. Specific increases in motor neuron excitability have been seen in neonatal ALS model mice, months before the onset of overt clinical symptoms (Quinlan et al., 2011). These changes seem to reflect alterations in intrinsic properties of motor neurons, because they can be observed in isolated embryonic neurons in culture. However, the gene differences underlying this hyperexcitability remain to be determined. If targets could be identified to modify motor neuron excitability, their modulation would potentially have early and potent effects.

More generally, calcium dysregulation is a frequently observed defect in models of ALS (reviewed in Grosskreutz et al., 2010). There is evidence from multiple sources for involvement of excitotoxicity, excessive $Ca^{++}$ influx through ionotropic glutamate receptors. This can result from defective glutamate reuptake, altered $Ca^{++}$ permeability of AMPA receptors by changes in subunit composition or RNA editing. Another site of calcium dysregulation is in mitochondria, which are strongly affected in the disease. In ALS models, mitochondria appear to be less able to handle large $Ca^{++}$ loads induced by electrical activity, leading to chronic $Ca^{++}$ overload. Lastly, the endoplasmic reticulum (ER) shows pathological changes at morphological and functional levels. ER stress is directly triggered by disease-causing mutations in vesicle-associate membrane protein-associated protein B (VAPB) and also by the unfolded protein response (UPR) observed in cells expressing misfolded mutant forms of SOD1. The shuttling of $Ca^{++}$ between the ER and mitochondria, called the ER-mitochondria $Ca^{++}$ cycle (ER-MCC), is therefore a potentially important site of dysfunction in ALS. However, much remains to be learned of the ways in which it is specifically affected in ALS motor neurons.

Accordingly, there is, inter alia, a need to identify agents for the treatment and amelioration of ALS. The present invention is directed towards meeting this and other needs.

SUMMARY OF THE INVENTION

One embodiment of the present invention is a method for identifying a candidate agent that may be effective to treat or ameliorate an effect of a neurodegenerative disease in a subject. This method comprises:
   (a) contacting a wildtype neuron and a mutant neuron with a stressor which is effective to accelerate the degeneration of the mutant neuron;
   (b) further contacting the wildtype neuron and the mutant neuron from step (a) with a candidate agent; and
   (c) determining whether the candidate agent lowers a wildtype to mutant survival ratio or increases both wildtype and mutant neuron survival,
wherein a candidate agent that lowers the wildtype to mutant survival ratio or increases both wildtype and mutant neuron survival indicates that the candidate agent may be effective to treat or ameliorate the effects of a neurodegenerative disease.

Another embodiment of the present invention is a candidate agent identified according to any method of the present invention.

A further embodiment of the present invention is a kit for identifying a candidate agent that may be effective to treat or ameliorate an effect of a neurodegenerative disease in a subject. This kit comprises a wildtype neuron, a mutant neuron, and a stressor which is effective to accelerate the degeneration of the mutant neuron.

Another embodiment of the present invention is a method for treating or ameliorating an effect of a neurodegenerative disease in a subject in need thereof. This method comprises administering to the subject an effective amount of an agent selected from the group consisting of dorsomorphin, PD407824, Ro 31-8220, pharmaceutically acceptable salts thereof, and combinations thereof.

A further embodiment of the present invention is a pharmaceutical composition for treating or ameliorating an effect of a neurodegenerative disease in a subject in need thereof. This pharmaceutical composition comprises a pharmaceutically acceptable carrier and an agent selected from the group consisting of dorsomorphin, PD407824, Ro 31-8220, pharmaceutically acceptable salts thereof, and combinations thereof.

An additional embodiment of the present invention is a kit for treating or ameliorating an effect of a neurodegenerative disease in a subject in need thereof. This kit comprises an agent selected from the group consisting of dorsomorphin, PD407824, Ro 31-8220, pharmaceutically acceptable salts thereof, and combinations thereof, packaged together with instructions for their use.

Another embodiment of the present invention is a method of increasing neuron survival. This method comprises contacting a neuron with an effective amount of an agent selected from the group consisting of dorsomorphin, PD407824, Ro 31-8220, pharmaceutically acceptable salts thereof, and combinations thereof.

BRIEF DESCRIPTION OF THE DRAWINGS

FIG. 1A shows a schematic as well as microscopic images of cells representative of the motor neurons differentiated from Hb9-RFP hSOD1$^{wt}$ and Hb9-GFP hSOD1$^{G93A}$ ES cell lines. These cell lines were employed for the two-color screen set forth in more detail below. FIG. 1B shows concentration dependent selective toxicity of certain identified stressors to ALS motor neurons. FIG. 1C shows the cell autonomous toxicity of CPA to FACS purified ALS and wildtype (WT) motor neurons.

FIG. 2A shows that CPA and thapsigargin are potent and specific blockers of SERCA $Ca^{++}$ pump in ER. FIGS. 2B and 2C show Fura-2 imaging of $Ca^{++}$ influx and buffering following kainate (KA) and CPA treatment of control and ALS motor neurons. FIG. 2D shows that a subset of ALS motor neurons exhibit increased $Ca^{++}$ release (peak value) from ER stores following CPA treatment.

FIG. 3A shows that Hb9-RFP (red fluorescent protein driven by the Hb9 promoter) lentivirus marks human embryonic stem cell derived motor neurons (ESC-MNs) expressing ISL1. FIG. 3B shows a fluorescence-activated cell sorting (FACS) profile and gate for sorting human ESC-MNs transduced with the lentivirus. FIG. 3C shows an image of a whole well of 96 well plate seeded with sorted human ESC-MNs acquired using a Plate Runner imager. FIG. 3D shows that sorted human ESC-MNs exhibit typical dependence on neurotrophic (NTFs) support for 7 day survival.

FIG. 4A shows that progressive denervation of neuromuscular junctions (NMJs) in the fast TA muscle is delayed by 100 days in the absence of MMP-9 (−/−) and by 60 days in the presence of a single allele (+/−). FIG. 4B shows that AAV-shRNA to MMP-9 administered intracerebroventricular (i.c.v.) (the 4$^{th}$ bar) or intramuscular (i.m.) (the 5$^{th}$ bar) delays denervation to the same extent as heterozygote deletions. FIG. 4C shows that CMAP measurements at P50 confirm the functionality of the preserved innervation. FIG. 4D shows that lifespan is also significantly prolonged by reductions of MMP-9 levels.

DETAILED DESCRIPTION OF THE INVENTION

Figure 1:
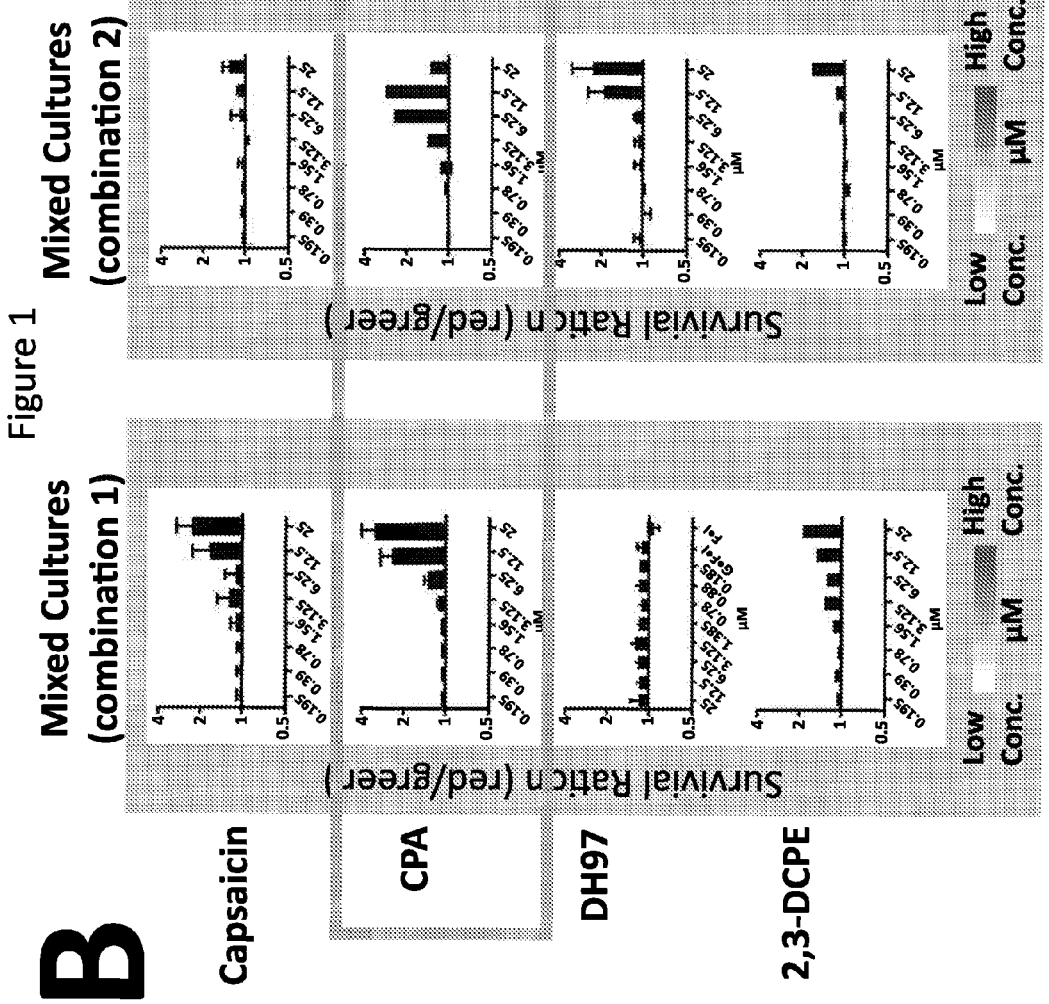
FIG. 1 shows a screen for compounds that are preferentially toxic to ALS motor neurons.
Figure 1:
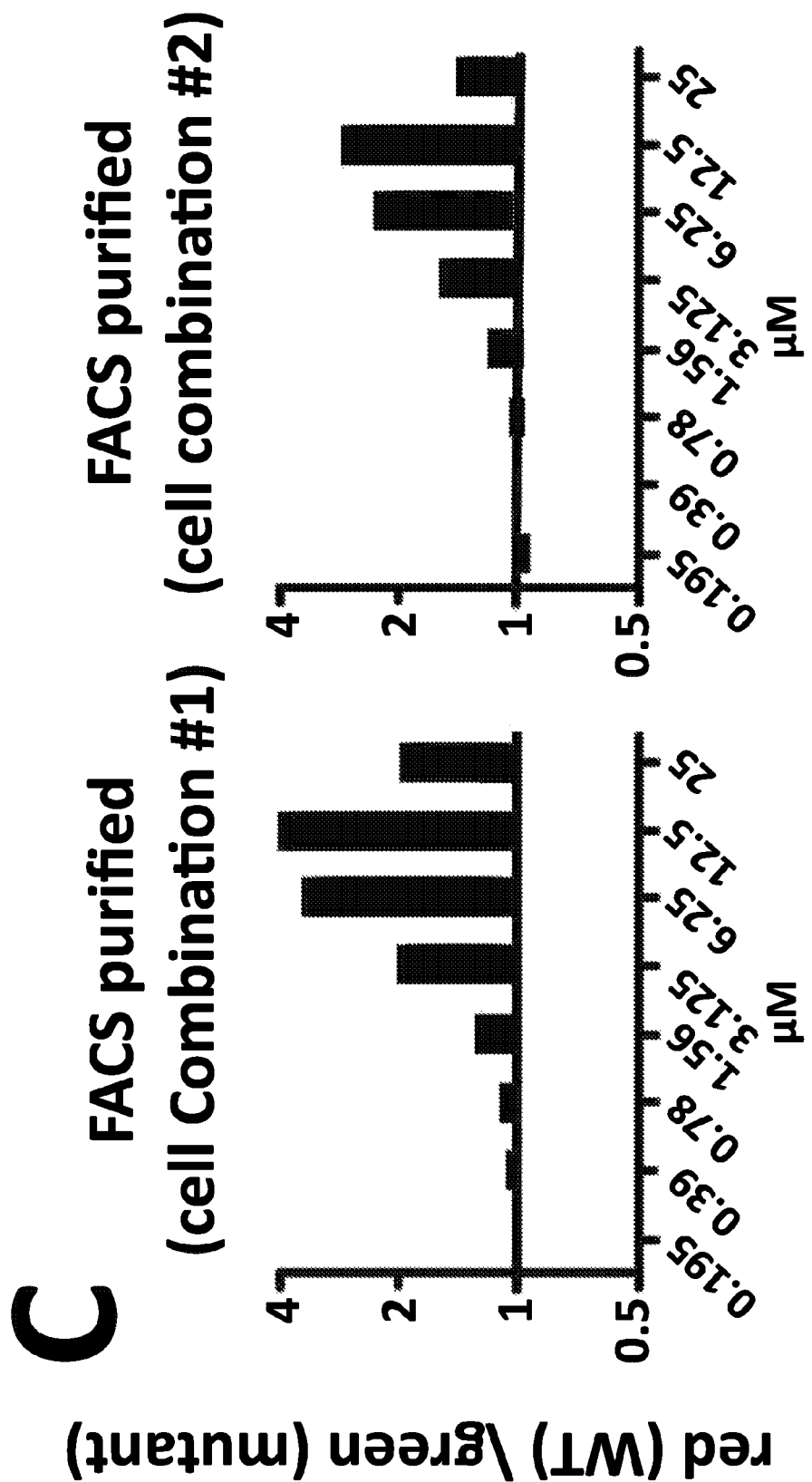

One embodiment of the present invention is a method for identifying a candidate agent that may be effective to treat or ameliorate an effect of a neurodegenerative disease in a subject. This method comprises:
(a) contacting a wildtype neuron and a mutant neuron with a stressor which is effective to accelerate the degeneration of the mutant neuron;
(b) further contacting the wildtype neuron and the mutant neuron from step (a) with a candidate agent; and
(c) determining whether the candidate agent lowers a wildtype to mutant survival ratio or increases both wildtype and mutant neuron survival, wherein a candidate agent that lowers the wildtype to mutant survival ratio or increases both wildtype and mutant neuron survival indicates that the candidate agent may be effective to treat or ameliorate the effects of a neurodegenerative disease.

Non-limiting examples of neurodegenerative diseases according to the present invention include Alzheimer's disease, Parkinson's disease, amyotrophic lateral sclerosis (ALS), Friedreich's ataxia, multiple sclerosis, Huntington's Disease, transmissible spongiform encephalopathy, Charcot-Marie-Tooth disease, dementia with Lewy bodies, corticobasal degeneration, progressive supranuclear palsy, and hereditary spastic paraparesis. Preferably, the neurodegenerative disease is ALS.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the candidate agents of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or, e.g., patient population. Accordingly, a given subject or, e.g., patient population may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present invention include, for example, agricultural animals, veterinary animals, laboratory animals, etc. Some examples of agricultural animals include cows, pigs, horses, goats, etc. Some examples of veterinary animals include dogs, cats, etc. Some examples of laboratory animals include rats, mice, rabbits, guinea pigs, etc.

In one aspect of this embodiment, the wildtype or the mutant neuron is a motor neuron. Preferably, the wildtype or the mutant neuron is a mammalian neuron. More preferably, the wildtype or the mutant neuron is a mouse neuron or a human neuron. Methods of generating the neuron are known in the art and are disclosed herein. For example, the neuron may be generated in vitro from embryonic stem cells. Alternatively, the neuron may be an induced pluripotent stem (iPS) cell-derived motor neuron (iPS-MN).

The candidate agent may be a biologic or a chemical. As used herein, a "biologic" means a substance which is derived from or produced by a living organism or synthesized to mimic an in vivo-derived agent or a derivative or product thereof. A biologic may be, for example, a nucleic acid, a polypeptide, or a polysaccharide. Preferably, the biologic is a nucleic acid, a protein, or a combination thereof. More preferably, the nucleic acid comprises an shRNA.

As used herein, a "chemical" means a substance that has a definite chemical composition and characteristic properties and that is not a biologic. Non-limiting examples of chemicals include small organic compounds and small inorganic compounds.

As used herein, a "wildtype" neuron means a neuron that does not contain changes in its gene that are associated with a neurodegenerative disease, such as ALS. In contrast, a "mutant" neuron for purposes of the present invention means a neuron that contains such a mutation. For example, certain mutations in the gene encoding superoxide dismutase 1 (SOD1), such as the G93A mutation, are known to be associated with the development of ALS. Thus, non-limiting examples of mutant neurons include those that contain SOD1 mutations, especially SOD1-G93A mutations. Mutant neurons within the scope of the present invention include such SOD1 mutations.

As used herein, a "stressor which is effective to accelerate the degeneration of the mutant neuron" means that a stressor, which may be a chemical or a biologic, upon contact with the neurons, is able to induce a decrease in the survival of the mutant neurons relative to the wildtype neurons, such as demonstrating a wildtype to mutant survival ratio of greater than 1.6 fold after 48 hours to 72 hours of contact, for example 1.6-1.75 folds after 48 hours of contact. Non-limiting examples of a stressor according to the present invention include an agonist of the TRPV2 receptor, a sarco(endo)-plasmic reticulum $Ca^{++}$-ATPase (SERCA) inhibitor, a MT2 melatonin receptor inhibitor, and a Bcl-xL inhibitor. Preferably, the stressor is a SERCA inhibitor, such as cyclopiazonic acid (CPA) and/or thapsigargin.

As used herein, an "agonist" means an agent that binds to a receptor of a cell and increases the activity of such a receptor. As used herein, an "inhibitor" means an agent that reduces the activity or the expression of a certain protein or the gene for that protein. Inhibitor includes antagonists of a receptor.

As used herein, "a wildtype to mutant survival ratio" means the ratio of the number of wildtype neurons divided by the number of mutant neurons. Preferably, a candidate agent of the present invention lowers the wildtype to mutant survival ratio from about 1.6-1.75 to below about 1.2 after 48 to 72 hours in culture.

As used herein, "increasing both wildtype and mutant neuron survival" means increasing the absolute number of live wildtype and mutant neurons.

In a further aspect of this embodiment, the wildtype neuron and the mutant neuron may be labeled differently. As used herein, a "label" is an entity which is detectable in its natural state. Methods of labeling cells are known in the art and are disclosed herein. For example, where the label is a colored particle, such as dye sols, metallic sols (e.g. colloidal gold), and colored latex particles, this may be visible to the naked eye, or become visible with the aid of an optical filter. Where the label is a fluorescent label, this may be subjected to applied stimulation, e.g. UV light to promote fluorescence. Suitable labels according to the present invention include various enzymes, prosthetic groups, fluorescent materials, luminescent materials and radioactive materials. Exemplary fluorescent detectable agents include fluorescein, fluorescein isothiocyanate, rhodamine, 5-dimethylamine-1-napthalenesulfonyl chloride, phycoerythrin and the like. Detectable enzymes, such as alkaline phosphatase, horseradish peroxidase, glucose oxidase and the like, may also be used. In the present invention, cells may also be labeled with biotin, and detected through indirect measurement of avidin or streptavidin binding. An example of a luminescent label includes luminol; and examples of suitable radioactive labels include $^{3}H$, $^{14}C$, $^{35}S$, $^{99}TC$, $^{125}I$, $^{131}I$, or $^{153}Sm$. More preferably, the neurons may be labeled with different types of fluorescent proteins. For example, a wildtype neuron may be labeled with a red fluorescent protein, and the mutant neuron may be labeled with a green fluorescent protein.

Methods of detecting such labels are well known to those of skill in the art and are disclosed herein. For example, radiolabels may be detected using photographic film or scintillation counters, fluorescent labels may be detected using a photo detector to detect emitted illumination. Enzymatic labels are typically detected by providing the enzyme with a substrate and detecting the reaction product produced by the action of the enzyme on the substrate. For example, when a detectable agent, such as, e.g., horseradish peroxidase (HRP) is present the addition of hydrogen peroxide and diaminobenzidine leads to a colored reaction product, which is detectable.

Another embodiment of the present invention is a candidate agent identified according to any method disclosed herein.

A further embodiment of the present invention is a kit for identifying a candidate agent that may be effective to treat or ameliorate an effect of a neurodegenerative disease in a subject. This kit comprises a wildtype neuron, a mutant neuron, and a stressor which is effective to accelerate the degeneration of the mutant neuron. Suitable wildtype neurons, mutant neurons, and stressors are as disclosed herein. The kit may further include other reagents including culture media, buffers, and the like as well as various vessels for carrying out the screening assay. The kit may also include instructions for carrying out the screening assay and any convenient packaging for convenient transport and storage of the kit.

Another embodiment of the present invention is a method for treating or ameliorating an effect of a neurodegenerative disease in a subject in need thereof. This method comprises administering to the subject, preferably a human in need thereof, an effective amount of an agent selected from the group consisting of dorsomorphin, PD407824 (9-hydroxy-4-phenyl-pyrrolo[3,4c]carbazole-1,3(2H,6H)-dione (Tocris Bioscience)), Ro 31-8220 3-[3-[2,5-Dihydro-4-(1-methyl-1H-indol-3-yl)-2,5-dioxo-1H-pyrrol-3-yl]-1H-indol-1-yl] propyl carbamimidothioic acid ester (Tocris Biosciences)), pharmaceutically acceptable salts thereof, and combinations thereof. For instance, one non-limiting example of a pharmaceutically acceptable salt of Ro 31-8220 is Ro 31-8220 mesylate.

Suitable and preferred subjects and neurodegenerative diseases are as disclosed herein.

A further embodiment of the present invention is a pharmaceutical composition for treating or ameliorating an effect of a neurodegenerative disease in a subject in need thereof. This pharmaceutical composition comprises a pharmaceutically acceptable carrier and an agent selected from the group consisting of dorsomorphin, PD407824, Ro 31-8220, pharmaceutically acceptable salts thereof, and combinations thereof.

Suitable and preferred subjects and neurodegenerative diseases are as disclosed herein.

An additional embodiment of the present invention is a kit for treating or ameliorating an effect of a neurodegenerative disease in a subject in need thereof. This kit comprises an agent selected from the group consisting of dorsomorphin, PD407824, Ro 31-8220, pharmaceutically acceptable salts thereof, and combinations thereof, packaged together with instructions for their use.

The kits according to the present invention may also include suitable storage containers, e.g., ampules, vials, tubes, etc., for each agent, e.g., pharmaceutical composition and other reagents, e.g., buffers, balanced salt solutions, etc., for use in administering the pharmaceutical compositions to subjects. The pharmaceutical compositions and other reagents may be present in the kits in any convenient form, such as, e.g., in a solution or in a powder form. The kits may further include instructions for use of the pharmaceutical compositions. The kits may further include a packaging container, optionally having one or more partitions for housing the pharmaceutical composition and other optional reagents. The kits may further include medical devices, e.g., syringes, IV bags, tubing, etc., for facilitating delivery to the subject.

Suitable and preferred subjects and neurodegenerative diseases are as disclosed herein.

Another embodiment of the present invention is a method of increasing neuron survival. This method comprises contacting the neuron with an effective amount of an agent selected from the group consisting of dorsomorphin, PD407824, Ro 31-8220, pharmaceutically acceptable salts thereof, and combinations thereof.

The neuron may be a wildtype neuron or a mutant neuron. The neuron may also be from a subject that has a neurodegenerative disease as disclosed herein, preferably ALS. The neuron may also be a motor neuron. Preferably, the neuron is a mammalian neuron. More preferably, the neuron is a mouse neuron or a human neuron.

In the present invention, an "effective amount" or a "therapeutically effective amount" of an agent, such as, e.g., a compound or pharmaceutical composition disclosed herein, is an amount of such agent, e.g., compound or pharmaceutical composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of an agent according to the invention will be that amount of the agent, which is the lowest dose effective to produce the desired effect. The effective dose of an agent, e.g., compound or composition of the present invention, may be administered as two, three, four, five, six or more sub-doses, administered separately at appropriate intervals throughout the day.

A suitable, non-limiting example of a dosage of an agent disclosed herein is from about 1 mg/kg to about 2400 mg/kg per day, such as from about 1 mg/kg to about 1200 mg/kg per day, 75 mg/kg per day to about 300 mg/kg per day, including from about 1 mg/kg to about 100 mg/kg per day. Other representative dosages of such agents include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of an agent disclosed herein may be administered as two, three, four, five, six or more sub-doses, administered separately at appropriate intervals throughout the day.

The agents or the pharmaceutical compositions of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, the agents or the pharmaceutical compositions of the present invention may be administered in conjunction with other treatments. The agents or the pharmaceutical compositions of the present invention may be encapsulated or otherwise protected against gastric or other secretions, if desired.

The pharmaceutical compositions of the invention may comprise one or more active agents or ingredients in admixture with one or more pharmaceutically-acceptable carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21$^{st}$ Edition, Lippincott Williams and Wilkins, Philadelphia, Pa.).

Pharmaceutically acceptable carriers are well known in the art (see, e.g., Remington, The Science and Practice of Pharmacy (21$^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The pharmaceutical compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

The pharmaceutical compositions of the present invention for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. The pharmaceutical compositions of the present invention which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

The pharmaceutical compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Additional Definitions

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

Nucleic Acid

"Nucleic acid" or "oligonucleotide" or "polynucleotide" used herein mean at least two nucleotides covalently linked together. Many variants of a nucleic acid may be used for the same purpose as a given nucleic acid. Thus, a nucleic acid also encompasses substantially identical nucleic acids and complements thereof.

Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

The nucleic acid may also be a RNA such as a mRNA, tRNA, short hairpin RNA (shRNA), short interfering RNA (sRNA), double-stranded RNA (dsRNA), transcriptional gene silencing RNA (ptgsRNA), Piwi-interacting RNA, pri-miRNA, pre-miRNA, micro-RNA (miRNA), or anti-miRNA, as described, e.g., in U.S. patent application Ser. Nos. 11/429,720, 11/384,049, 11/418,870, and 11/429,720 and Published International Application Nos. WO 2005/116250 and WO 2006/126040.

sRNA gene-targeting may be carried out by transient sRNA transfer into cells, achieved by such classic methods as lipid-mediated transfection (such as encapsulation in liposome, complexing with cationic lipids, cholesterol, and/or condensing polymers, electroporation, or microinjection). sRNA gene-targeting may also be carried out by administration of sRNA conjugated with antibodies or sRNA complexed with a fusion protein comprising a cell-penetrating peptide conjugated to a double-stranded (ds) RNA-binding domain (DRBD) that binds to the sRNA (see, e.g., U.S. Patent Application Publication No. 2009/0093026).

An shRNA molecule has two sequence regions that are reversely complementary to one another and can form a double strand with one another in an intramolecular manner. shRNA gene-targeting may be carried out by using a vector introduced into cells, such as viral vectors (lentiviral vectors, adenoviral vectors, or adeno-associated viral vectors for example).

The nucleic acid may also be an aptamer, an intramer, or a spiegelmer. The term "aptamer" refers to a nucleic acid or oligonucleotide molecule that binds to a specific molecular target. Aptamers are derived from an in vitro evolutionary process (e.g., SELEX (Systematic Evolution of Ligands by EXponential Enrichment), disclosed in U.S. Pat. No. 5,270, 163), which selects for target-specific aptamer sequences from large combinatorial libraries. Aptamer compositions may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'—OH group of a ribonucleotide may be replaced by 2'-F or 2'-$NH_2$), which may improve a desired property, e.g., resistance to nucleases or longer lifetime in blood. Aptamers may be conjugated to other molecules, e.g., a high molecular weight carrier to slow clearance of the aptamer from the circulatory system. Aptamers may be specifically cross-linked to their cognate ligands, e.g., by photo-activation of a cross-linker (Brody, E. N. and L. Gold (2000) J. Biotechnol. 74:5-13).

The term "intramer" refers to an aptamer which is expressed in vivo. For example, a vaccinia virus-based RNA expression system has been used to express specific RNA aptamers at high levels in the cytoplasm of leukocytes (Blind, M. et al. (1999) Proc. Natl. Acad. Sci. USA 96:3606-3610).

The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides.

A nucleic acid will generally contain phosphodiester bonds, although nucleic acid analogs may be included that may have at least one different linkage, e.g., phosphoramidate, phosphorothioate, phosphorodithioate, or O-methyl-phosphoroamidite linkages and peptide nucleic acid backbones and linkages. Other analog nucleic acids include those with positive backbones; non-ionic backbones, and non-ribose backbones, including those disclosed in U.S. Pat. Nos. 5,235,033 and 5,034,506. Nucleic acids containing one or more non-naturally occurring or modified nucleotides are also included within the definition of nucleic acid. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as disclosed in Krutzfeldt et al., Nature (Oct. 30, 2005), Soutschek et al., Nature 432:173-178 (2004), and U.S. Patent Application Publication No.

20050107325. Modified nucleotides and nucleic acids may also include locked nucleic acids (LNA), as disclosed in U.S. Patent Application Publication No. 20020115080. Additional modified nucleotides and nucleic acids are disclosed in U.S. Patent Application Publication No. 20050182005. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

Peptide, Polypeptide, Protein

The terms "peptide," "polypeptide," and "protein" are used interchangeably herein. In the present invention, these terms mean a linked sequence of amino acids, which may be natural, synthetic, or a modification, or combination of natural and synthetic. The term includes antibodies, antibody mimetics, domain antibodies, lipocalins, targeted proteases, and polypeptide mimetics. The term also includes vaccines containing a peptide or peptide fragment intended to raise antibodies against the peptide or peptide fragment.

"Antibody" as used herein includes an antibody of classes IgG, IgM, IgA, IgD, or IgE, or fragments or derivatives thereof, including Fab, F(ab')2, Fd, and single chain antibodies, diabodies, bispecific antibodies, and bifunctional antibodies. The antibody may be a monoclonal antibody, polyclonal antibody, affinity purified antibody, or mixtures thereof which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety. The antibody may be a human or humanized antibody. These and other antibodies are disclosed in U.S. Published Patent Application No. 20070065447.

Other antibody-like molecules are also within the scope of the present invention. Such antibody-like molecules include, e.g., receptor traps (such as entanercept), antibody mimetics (such as adnectins, fibronectin based "addressable" therapeutic binding molecules from, e.g., Compound Therapeutics, Inc.), domain antibodies (the smallest functional fragment of a naturally occurring single-domain antibody (such as, e.g., nanobodies; see, e.g., Cortez-Retamozo et al., Cancer Res. 2004 Apr. 15; 64(8):2853-7)).

Suitable antibody mimetics generally can be used as surrogates for the antibodies and antibody fragments described herein. Such antibody mimetics may be associated with advantageous properties (e.g., they may be water soluble, resistant to proteolysis, and/or be nonimmunogenic). For example, peptides comprising a synthetic beta-loop structure that mimics the second complementarity-determining region (CDR) of monoclonal antibodies have been proposed and generated. See, e.g., Saragovi et al., Science. Aug. 16, 1991; 253(5021):792-5. Peptide antibody mimetics also have been generated by use of peptide mapping to determine "active" antigen recognition residues, molecular modeling, and a molecular dynamics trajectory analysis, so as to design a peptide mimic containing antigen contact residues from multiple CDRs. See, e.g., Cassett et al., Biochem Biophys Res Commun. Jul. 18, 2003; 307(1): 198-205. Additional discussion of related principles, methods, etc., that may be applicable in the context of this invention are provided in, e.g., Fassina, Immunomethods. October 1994; 5(2):121-9.

As used herein, "peptide" includes targeted proteases, which are capable of, e.g., substrate-targeted inhibition of post-translational modification such as disclosed in, e.g., U.S. Patent Application Publication No. 20060275823.

In the present invention, "peptide" further includes anticalins. Anticalins can be screened for agents that decrease the number of cancer stem cells. Anticalins are ligand-binding proteins that have been constructed based on a lipocalin scaffold (Weiss, G. A. and H. B. Lowman (2000) Chem. Biol. 7:R177-R184; Skerra, A. (2001) J. Biotechnol. 74:257-275). The protein architecture of lipocalins can include a beta-barrel having eight antiparallel beta-strands, which supports four loops at its open end. These loops form the natural ligand-binding site of the lipocalins, a site which can be re-engineered in vitro by amino acid substitutions to impart novel binding specificities. The amino acid substitutions can be made using methods known in the art, and can include conservative substitutions (e.g., substitutions that do not alter binding specificity) or substitutions that modestly, moderately, or significantly alter binding specificity.

In general, a polypeptide mimetic ("peptidomimetic") is a molecule that mimics the biological activity of a polypeptide, but that is not peptidic in chemical nature. While, in certain embodiments, a peptidomimetic is a molecule that contains no peptide bonds (that is, amide bonds between amino acids), the term peptidomimetic may include molecules that are not completely peptidic in character, such as pseudo-peptides, semi-peptides, and peptoids. Examples of some peptidomimetics by the broader definition (e.g., where part of a polypeptide is replaced by a structure lacking peptide bonds) are described below. Whether completely or partially non-peptide in character, peptidomimetics according to this invention may provide a spatial arrangement of reactive chemical moieties that closely resembles the three-dimensional arrangement of active groups in a polypeptide. As a result of this similar active-site geometry, the peptidomimetic may exhibit biological effects that are similar to the biological activity of a polypeptide.

There are several potential advantages for using a mimetic of a given polypeptide rather than the polypeptide itself. For example, polypeptides may exhibit two undesirable attributes, i.e., poor bioavailability and short duration of action. Peptidomimetics are often small enough to be both orally active and to have a long duration of action. There are also problems associated with stability, storage and immunoreactivity for polypeptides that may be reduced with peptidomimetics.

Polypeptides having a desired biological activity can be used in the development of peptidomimetics with similar biological activities. Techniques of developing peptidomimetics from polypeptides are known. Peptide bonds can be replaced by non-peptide bonds that allow the peptidomimetic to adopt a similar structure, and therefore biological activity, to the original polypeptide. Further modifications can also be made by replacing chemical groups of the amino acids with other chemical groups of similar structure, shape or reactivity. The development of peptidomimetics can be aided by determining the tertiary structure of the original polypeptide, either free or bound to a ligand, by NMR spectroscopy, crystallography and/or computer-aided molecular modeling. These techniques aid in the development of novel compositions of higher potency and/or greater bioavailability and/or greater stability than the original polypeptide (Dean (1994), BioEssays, 16: 683-687; Cohen and Shatzmiller (1993), J. Mol. Graph., 11: 166-173; Wiley and Rich (1993), Med. Res. Rev., 13: 327-384; Moore (1994), Trends Pharmacol. Sci., 15: 124-129; Hruby (1993), Biopolymers, 33: 1073-1082; Bugg et al. (1993), Sci. Am., 269: 92-98.

Polysaccharides

The term "polysaccharides" means polymeric carbohydrate structures, formed of repeating units (either mono- or di-saccharides) joined together by glycosidic bonds. The units of mono- or di-saccharides may be the same or different. Non-limiting examples of polysaccharides include starch, glycogen, cellulose, and chitin.

Small Organic or Inorganic Molecules

The phrase "small organic" or "small inorganic" molecule includes any chemical or other moiety, other than polysaccharides, polypeptides, and nucleic acids, that can act to affect biological processes. Small molecules can include any number of therapeutic agents presently known and used, or can be synthesized in a library of such molecules for the purpose of screening for biological function(s). Small molecules are distinguished from macromolecules by size. The small molecules of this invention usually have a molecular weight less than about 5,000 daltons (Da), preferably less than about 2,500 Da, more preferably less than 1,000 Da, most preferably less than about 500 Da.

As used herein, the term "organic compound" refers to any carbon-based compound other than biologics such as nucleic acids, polypeptides, and polysaccharides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, mono-saccharides, di-saccharides, amino acids, nucleosides, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles, and phenols. An organic compound as used herein also includes nitrated organic compounds and halogenated (e.g., chlorinated) organic compounds. Collections of small molecules, and small molecules identified according to the invention are characterized by techniques such as accelerator mass spectrometry (AMS; see Turteltaub et al., Curr Pharm Des 2000 6:991-1007, Bioanalytical applications of accelerator mass spectrometry for pharmaceutical research; and Enjalbal et al., Mass Spectrom Rev 2000 19:139-61, Mass spectrometry in combinatorial chemistry.)

Preferred small molecules are relatively easier and less expensively manufactured, formulated or otherwise prepared. Preferred small molecules are stable under a variety of storage conditions. Preferred small molecules may be placed in tight association with macromolecules to form molecules that are biologically active and that have improved pharmaceutical properties. Improved pharmaceutical properties include changes in circulation time, distribution, metabolism, modification, excretion, secretion, elimination, and stability that are favorable to the desired biological activity. Improved pharmaceutical properties include changes in the toxicological and efficacy characteristics of the chemical entity.

The following examples are provided to further illustrate the methods of the present invention. These examples are illustrative only and are not intended to limit the scope of the invention in any way.

EXAMPLES

Example 1

Two-color Screen for Agents that Preferentially Trigger Degeneration of ALS Motor Neurons Given the failure of other groups to identify a spontaneous ALS-related motor neuron phenotype in cultures of patient-derived iPS-MNs, the inventors reasoned that the identification of stressors to which ALS motor neurons are preferentially vulnerable would have two advantages. First, it would provide insights into the functional differences between ALS and control motor neurons, and therefore potentially into the first changes underlying degeneration during the disease. Second, the selective degeneration of motor neurons thus induced could be used as an assay for candidate neuroprotective treatments. To achieve these goals, mouse embryonic stem cell-derived motor neurons (ES-MNs) were first used, because these are relatively easy to generate in large numbers at high abundance (about 40% of all cells in the culture are motor neurons).

Multiple ES cell lines from SOD1$^{G93A}$ mice that had been bred to a reporter strain expressing GFP under the motor neuron-specific Hb9 promoter were generated. ES cells from mice overexpressing wildtype human SOD1 (SOD1$^{WT}$) bred to mice expressing a new Hb9::RFP reporter (K. C. Kanning, unpublished) were used as controls. When differentiated in vitro using retinoic acid and an agonist of the sonic hedgehog pathway, these ES cells therefore generated green ALS motor neurons and red controls (FIG. 1A). By mixing these in equal numbers in culture, the response of ALS and control motor neurons to otherwise identical culture conditions could be quantified. This approach would reduce noise due to differences in individual culture wells, seeding density, position in incubator, etc., and that the ratio between numbers of WT and G93A cells would be a sensitive measure of selective vulnerability. In the presence of an agent that showed no effect or indiscriminate neurotoxicity, it would remain close to 1, but following treatment with a drug that preferentially kills ALS motor neurons, the ratio would be significantly higher.

Figure 2:
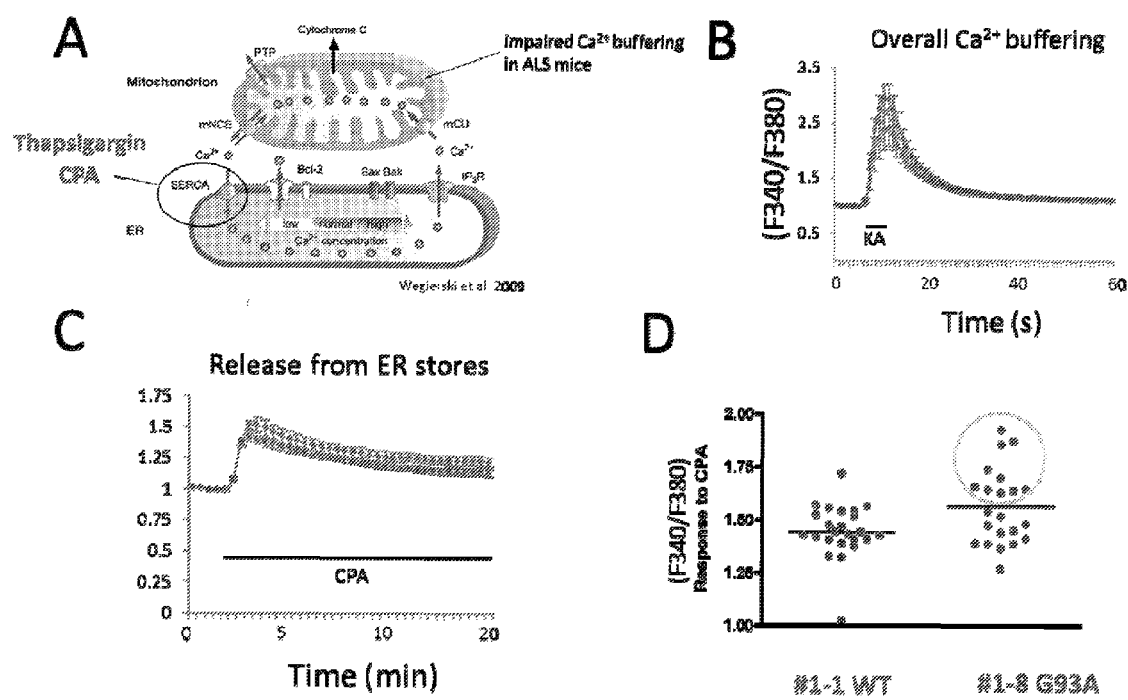
FIG. 2 shows the effects of SERCA blockers on $Ca^{++}$ handling in motor neurons.

Using this assay miniaturized to a 96-well format, it was confirmed that after 3 days in either the presence or absence of a cocktail of neurotrophic factors, there was only a subtle decrease in ALS motor neuron survival relative to controls. An open-ended screen of the Tocriscreen Mini and Custom collection library of bioactive compounds was therefore performed to identify agents of known mechanism that could selectively induce death of ALS motor neurons. A total of 1,275 compounds were screened initially at a single concentration (10 µM), and those that were deemed too toxic were retested at 1 µM. A total of 19 compounds showed WT/G93A ratios that were >1.6-fold (corresponding to a hit frequency of 1.5%). Retesting of independently sourced compounds reduced the total number of hits to 9. Preferential activity on ALS motor neurons was subsequently confirmed for 4 of the hits using an independent pair of WT and G93A lines (FIG. 1B). The active compounds were: (a) capsaicin, an agonist of the TRPV2 receptor that is predominantly expressed on sensory neurons, (b) CPA (cyclopiazonic acid), which is an inhibitor of SERCA (sarco(endo)-plasmic reticulum Ca$^{++}$-ATPase) pumps, which sequester Ca$^{++}$ into the ER from the cytoplasm in an ATP-dependent manner (FIG. 2A), (c) DH97, a potent MT2 melatonin receptor antagonist, and (d) 2,3-DCPE, a compound that selectively induces apoptosis and downregulates Bcl-xL expression in human cancer vs. normal cells in vitro. The inventors focused on CPA because it induced the most robust change in the WT/G93A ratio (>3 in both combinations of ES lines) and because of the relevance of its mechanism of action to the alterations in $Ca^{++}$ handling that are characteristic of ALS motor neurons.

We first asked whether the actions of CPA were direct on motor neurons, or mediated by other cell types present in the mixed culture used for screening. FACS-sorted ES-MNs of both pairs of WT and G93A lines showed robust preferential degeneration of ALS motor neurons in the presence of CPA, confirming that ALS motor neuron vulnerability was induced directly (FIG. 1C). The concentrations of CPA that were most potent in the assay were similar to those routinely used to block SERCA activity, but to further determine whether CPA was acting on its cognate target, another SERCA inhibitor, thapsigargin, was tested. It was found that thapsigargin triggered the death of 2- to 4-fold more ALS motor neurons than controls using concentrations at which it is known to block SERCA (on the order of 1 nM). Thus, degeneration induced by SERCA inhibition robustly differentiates between $SOD1^{G93A}$ and $SOD1^{WT}$ motor neurons. Neither thapsigargin nor CPA has gross effects on neuronal function. For example, they do not affect respiratory rhythm when applied to neurons of the pre-Botzinger complex (Beltran-Parrazal et al., 2012). This provides further support for the notion that the selective effect of SERCA inhibitors on ALS motor neurons is a function of the disease.

Example 2

Effects of CPA on $Ca^{++}$ Handling by ES-derived Motor Neurons

To explore potential mechanisms underlying the ALS-selective toxicity of CPA, calcium imaging in ES-MNs loaded with the calcium indicator dye Fura-2 was used. In preliminary experiments, rise and fall constants following a 5-second pulse of kainic acid were monitored, and no significant difference between the G93A and WT lines were found (FIG. 2B). These results suggest that there is not overall dysregulation of $Ca^{++}$ buffering in these embryonic motor neurons, in agreement with the similar spontaneous survival properties observed for WT and G93A motor neurons. It was hypothesized that CPA might selectively induce an imbalance in $Ca^{++}$ handling. To monitor release of $Ca^{++}$ from endoplasmic reticulum (ER) stores, ES-MNs of each genotype were incubated for 20 minutes with 10 µM CPA. An initial rapid increase of Fura-2 signal was followed by a slow recovery, as $Ca^{++}$ was sequestered by other routes, out of which mitochondria may be the main compensatory compartment. Although the recovery kinetics were indistinguishable between the two genotypes, the initial release was greater in about 40% of the G93A cells (greater than 20 ES-MNs imaged for each genotype in 3-4 independent experiments) (FIGS. 2C-D). These results suggest that CPA triggers an increased accumulation of $Ca^{++}$ in the cytoplasm in a subpopulation of ALS motor neurons, but not in controls, and may reflect the known $Ca^{++}$ buffering deficit in ALS mitochondria (Damiano et al., 2006).

Example 3

Techniques for Identification and Enrichment of Human iPS-MNs

Figure 3:
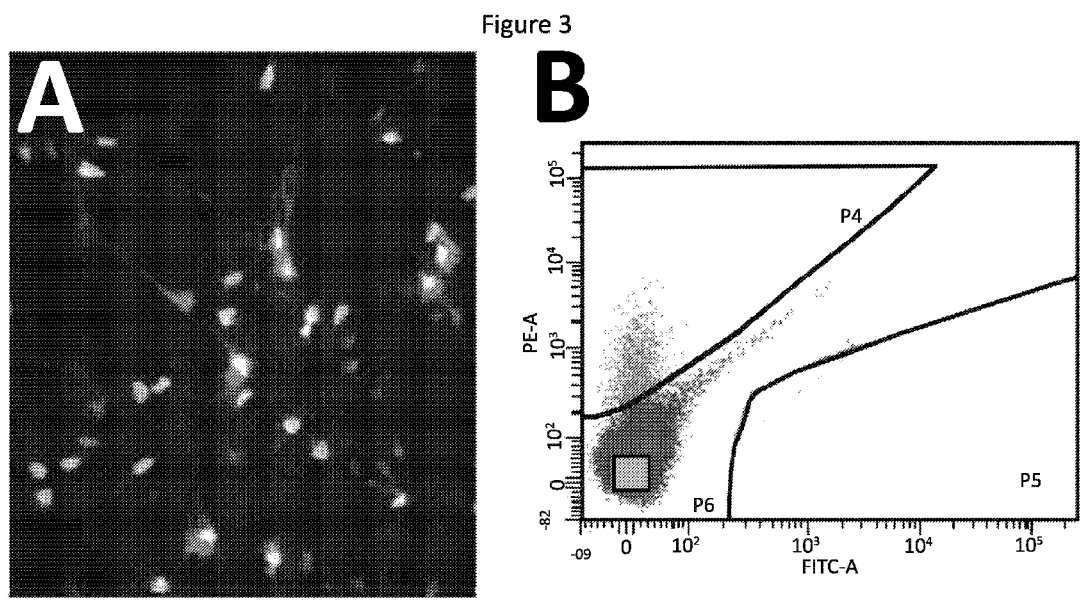
FIG. 3 shows the tools for enrichment and survival assays using human embryonic stem cell (ES) or induced pluripotent stem cell (iPS) derived motor neurons.
Figure 3:
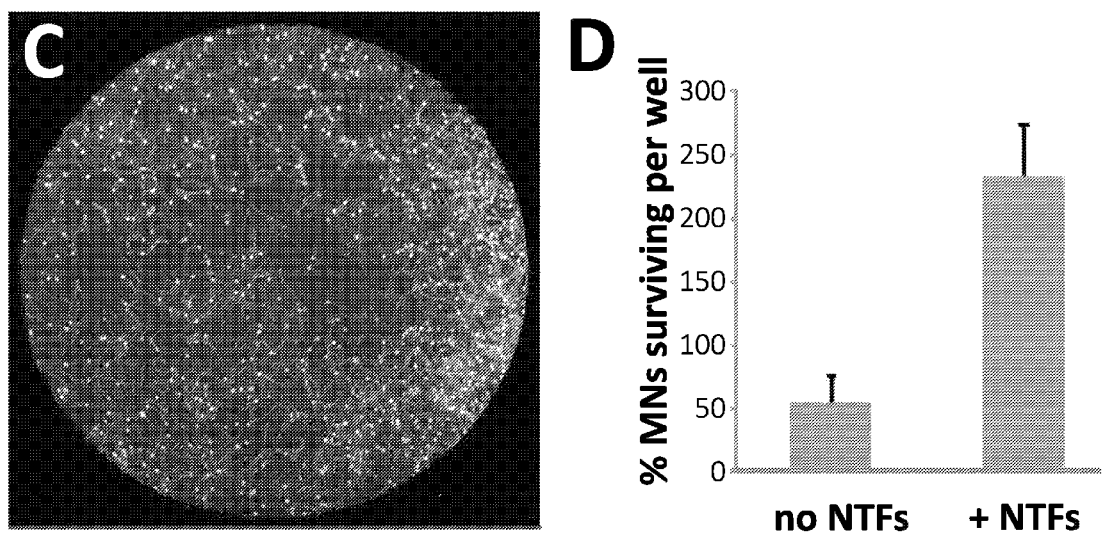

Labeled populations of iPS-MNs from human patients are necessary to perform precise electrophysiological and gene expression analyses on iPS-MNs. Using a construct that was a generous gift of C. Marchetto and F. Gage (Salk), a recombinant lentiviral system was used to label iPS-MNs following differentiation (FIG. 3). The vectors utilize a truncated 3.6 Kb segment of the mouse HB9 promoter to drive expression of tagRFP. Motor neuron specificity of the sHB9::RFP virus was confirmed by immunohistochemistry and expression analysis. hES-MN cultures were infected one day following differentiation with approximately 1 transducing unit of sHB9::RFP virus per cell and then allowed to mature for an additional 20 days. After maturation, cultures were immunostained for LVsHB9::RFP and motor neuron marker Islet1/2 (FIG. 3A). Viral RFP overlap with HB9::GFP and Islet1/2 was quantified using MetaMorph Multi-Wavelength Cell Scoring software: 75% of virally-labeled cells expressed motor neuron markers. In parallel, 3,000 LVsHB9::RFP positive cells were FACS sorted (FIG. 3B) and subjected to qPCR analysis to quantify levels of the motor neuron markers HB9, Islet1, and high-affinity choline transporter 1 (CHT1). All three markers showed 4- to 6-fold enrichment. Thus the short HB9 promoter viral tagging system is suitable for both histological and expression analysis of hES/iPS-derived motor neurons.

Example 4

Survival Assays Using Purified Human Stem Cell-derived Motor Neurons

Robust survival assays for human iPS-MNs are required for the studies. Mixed cultures of human stem cell-derived neurons present a major technical challenge for the design of robust cellular assays because of the neurogenesis that continues for many weeks. All the survival assays are therefore performed using purified motor neurons, a technique the inventors first developed using the stable reporter line HBG1, which expresses GFP under the control of the motor neuron-specific promoter Hb9 (generous gift from K. Eggan, Harvard). Motor neurons are large, fragile cells and have been considered to survive classical FACS sorting poorly. The FACS conditions were optimized for sorting so that Hb9::GFP motor neurons can be obtained in excellent condition.

Motor neurons were seeded in 96-well plates and cultured for 7 days before adding AM-calcein, a vital dye that results in a stronger signal than GFP autofluorescence. Furthermore, AM-calcein allows for the visualization of full-length cell processes, while GFP fluorescence in these cells is primarily limited to the cell body (FIG. 3C). Using this readout, we compared survival of human motor neurons in the presence and absence of neurotrophic factors and found a significant 5-fold difference between the two conditions (FIG. 3D). Thus, a robust system for measuring effects of modifiers on MN degeneration has been developed.

Example 5

Reduced Expression of SERCA Pumps by iPS-MNs from ALS Patients

Although widely expressed in spinal neurons including motor neurons (Allen Brain Atlas), SERCA subunits have been the subject of very little study in the CNS. The profiling data allowed for the estimation of expression of SERCA variants in the ALS and control groups. Human motor neurons expressed significant levels of only three splice variants: ATP2B1, ATP2B4 and ATP2C4, the second of which was also reported to be selectively expressed by primary rodent motor neurons (Van Den Bosch et al., 1999). Strikingly, levels of the first two were reduced by 20-35% in ALS ES-MNs compared to healthy controls, suggesting an intrinsic defect in $Ca^{++}$ buffering.

Example 6

Figure 4:
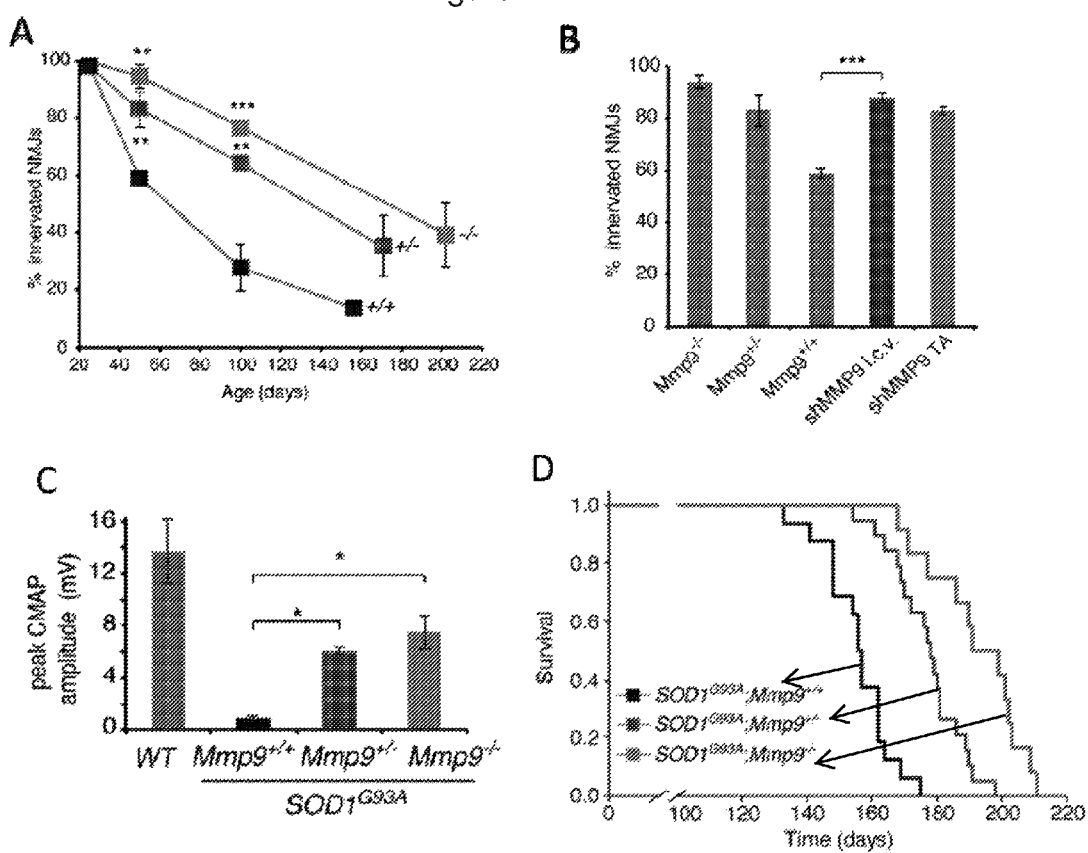
FIG. 4 shows the approaches and endpoints for measuring gene function in mutant SOD1 mice.

Robust Tools and Endpoints for Gain- and Loss-of-Function Studies in Mutant $SOD1^{G93A}$ Mice In Vivo AAV viral vectors, as well as breeding to knockout strains, may be used to modulate gene expression in ALS model mice in vivo. To demonstrate the feasibility of these approaches in our laboratory, we illustrate results concerning MMP-9 (matrix metalloproteinase-9). We had found that MMP-9 is selectively expressed in ALS-vulnerable subpopulations of motor neurons suggesting that it might contribute actively to disease onset or expression, and that mmp9 gene inactivation in $SOD1^{G93A}$ mice might confer benefit. We tested this hypothesis in two ways. First, mmp9 knockout mice were crossed to the $SOD1^{G93A}$ model. As our main endpoint, we focused on the earliest morphological change reported in these mice: denervation of fast muscle fibers (FIG. 4A). This endpoint is important in that it defines the clinical onset of paralysis and corresponds to findings in human patients with the sporadic form of the disease. The fast TA muscle is denervated early and extensively in control $SOD1^{G93A}$ mice. Strikingly, however, in the absence of MMP-9, we observed an approximate 3-month delay in denervation, the greatest effect yet reported in this model (FIG. 4A). This morphological preservation was reflected in a >50% protection of muscle force, as measured by compound muscle action potentials (CMAP; FIG. 4C). Median lifespan was increased by 39 days (or 25%) (FIG. 4D). Therefore, muscle denervation provides a robust and predictive assay for ALS disease modifiers.

We will use AAV vectors for GOF and LOF studies as an alternative to breeding to KO/Tg mice. We have already used two complementary techniques for gene delivery to motor neurons. First, intramuscular injection of AAV6 transduces not only the muscle but also a high percentage of the motor neurons in that pool. Second, a single neonatal i.c.v. injection of AAV6 virus leads to selective transduction of a majority of motor neurons, but of few other spinal cord cells (Towne and Aebischer, 2009). This relatively non-invasive procedure provides an exciting new means to target motor neurons without the need to generate new mouse strains or to inject multiple muscles. To test the requirement for MMP-9, we injected AAV6 encoding shRNA by each of the two routes into $SOD1^{G93A}$ mice at neonatal stages and quantified TA denervation at P50. Muscle innervation was significantly preserved, to an extent comparable to that provided by heterozygote germline deletion of mmp9. Thus AAV-shRNA constructs can be used to probe the requirement for candidate therapeutic targets in the ALS degenerative process even when knockout strains are not available.

Example 7

Figure 5:
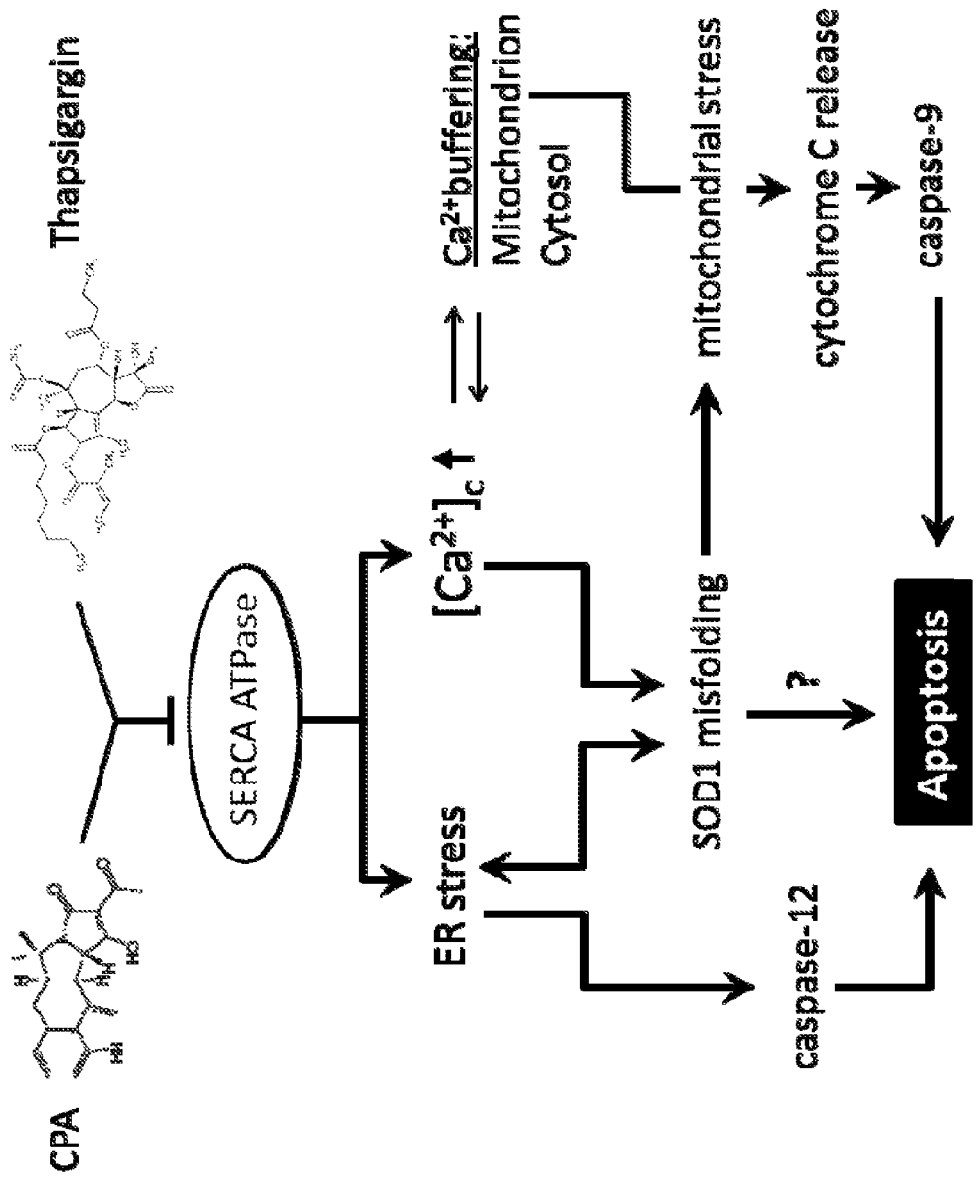
FIG. 5 shows a proposed mechanism of action of SERCA antagonists on ALS motor neurons
Figure 6:
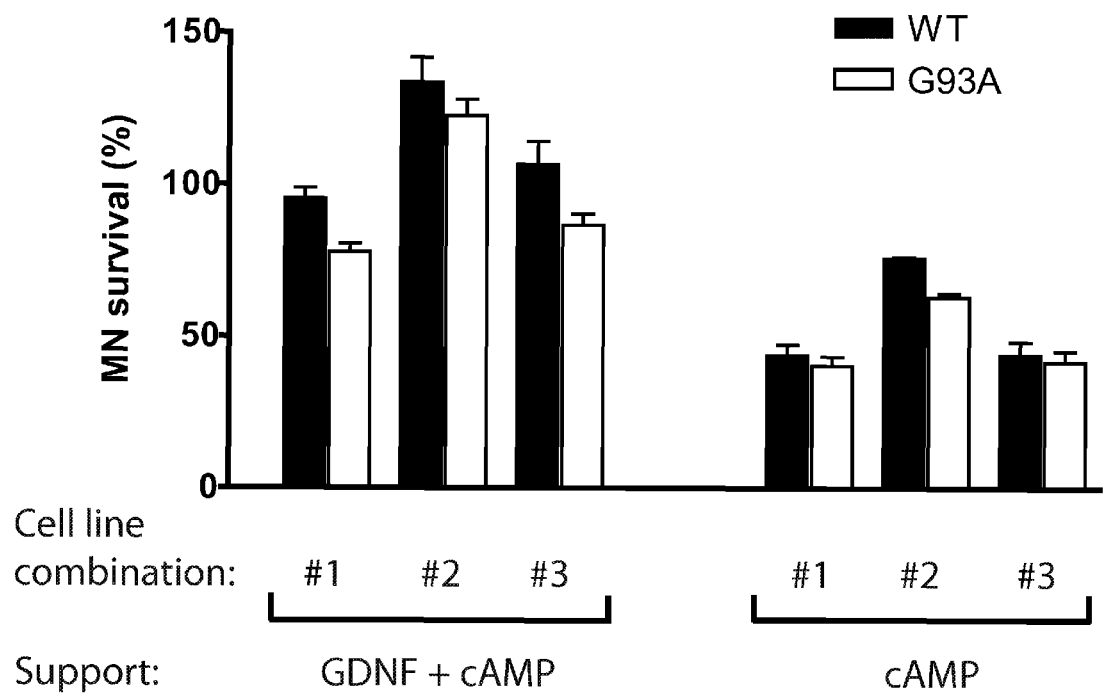
FIG. 6 shows the subtle survival phenotype of ALS motor neurons in vitro. When grown under either supportive or less supportive conditions, embryonic stem cell-derived motor neurons carrying the ALS-related G93A mutation show a subtle difference in survival. Bar graph shows surviving motor neurons at 3 days post plating for 3 different set of ALS and WT cell lines.
Figure 7:
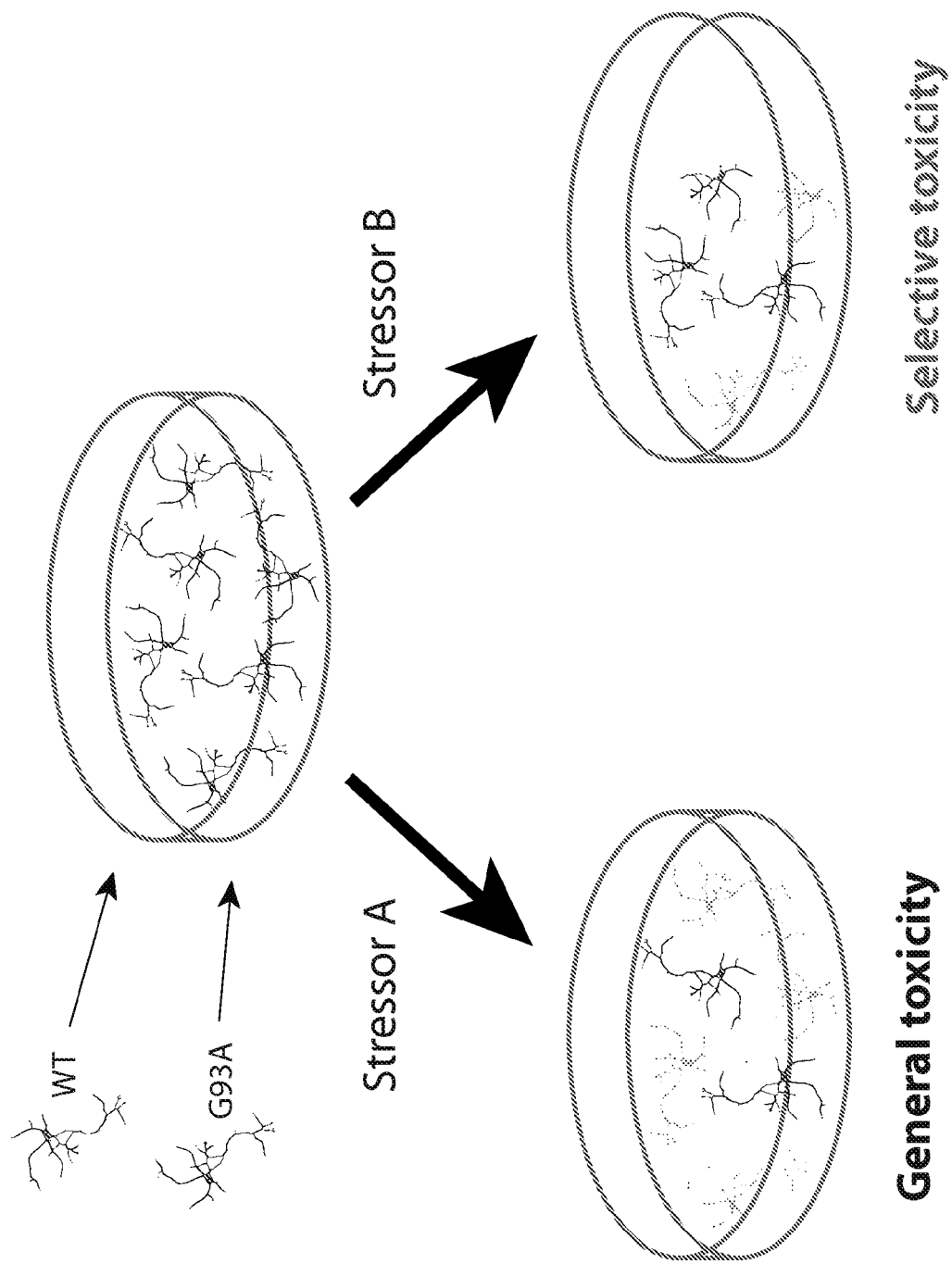
FIG. 7 is a schematic of a search for stressors mediating selective toxicity to ALS motor neurons. In order to identify biological stressors acting in synergy with SOD1 mutations, a dual color cell culture model in which WT and ALS (G93A) motor neurons were mixed at equal proportions was employed. It was expected that most stressors either have no effect or cause general toxicity, but certain stressors may cause selective degeneration of ALS motor neurons.
Figure 8:
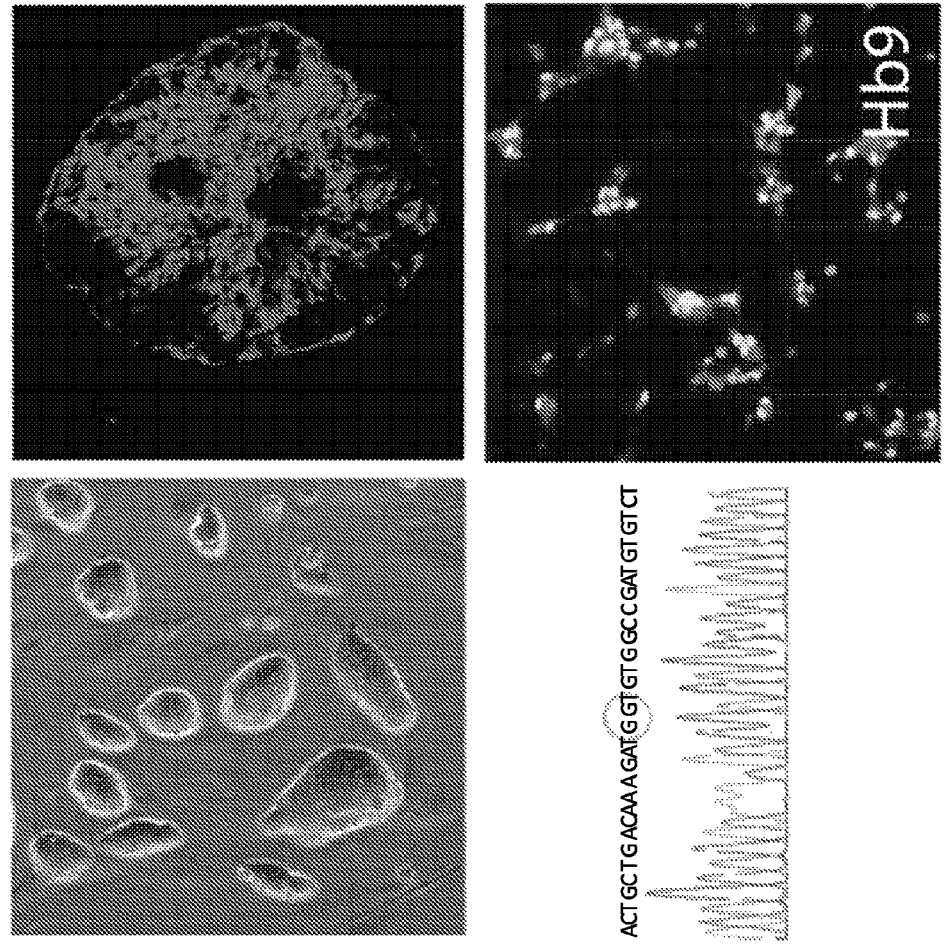
FIG. 8 show the tools used for a screen according to the present invention. Transgenic embryonic stem cell lines were derived from day 3.5 blastocysts. GFP and RFP motor neuron reporter lines were differentiated in suspension, sequenced to confirm the presence of human transgenes (FIG. 8A), and characterized with regard to differentiation efficiency and overlap between motor neuron markers and reporter (FIG. 8B).
Figure 8:
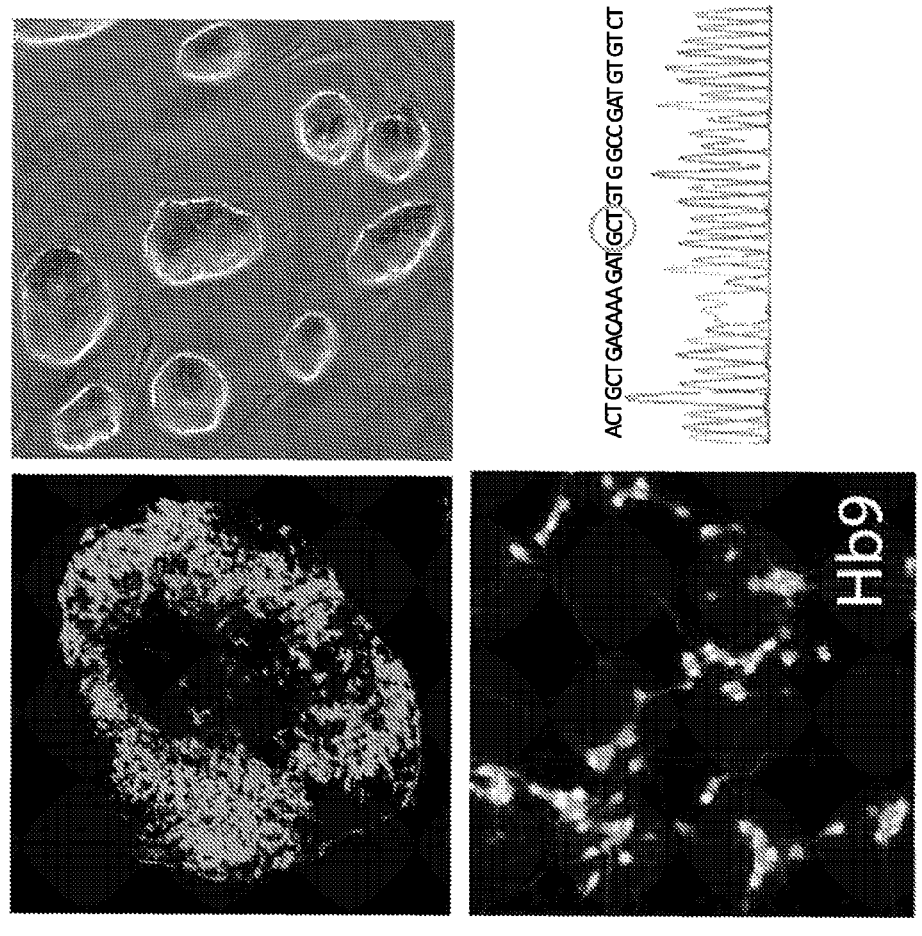
Figure 8:
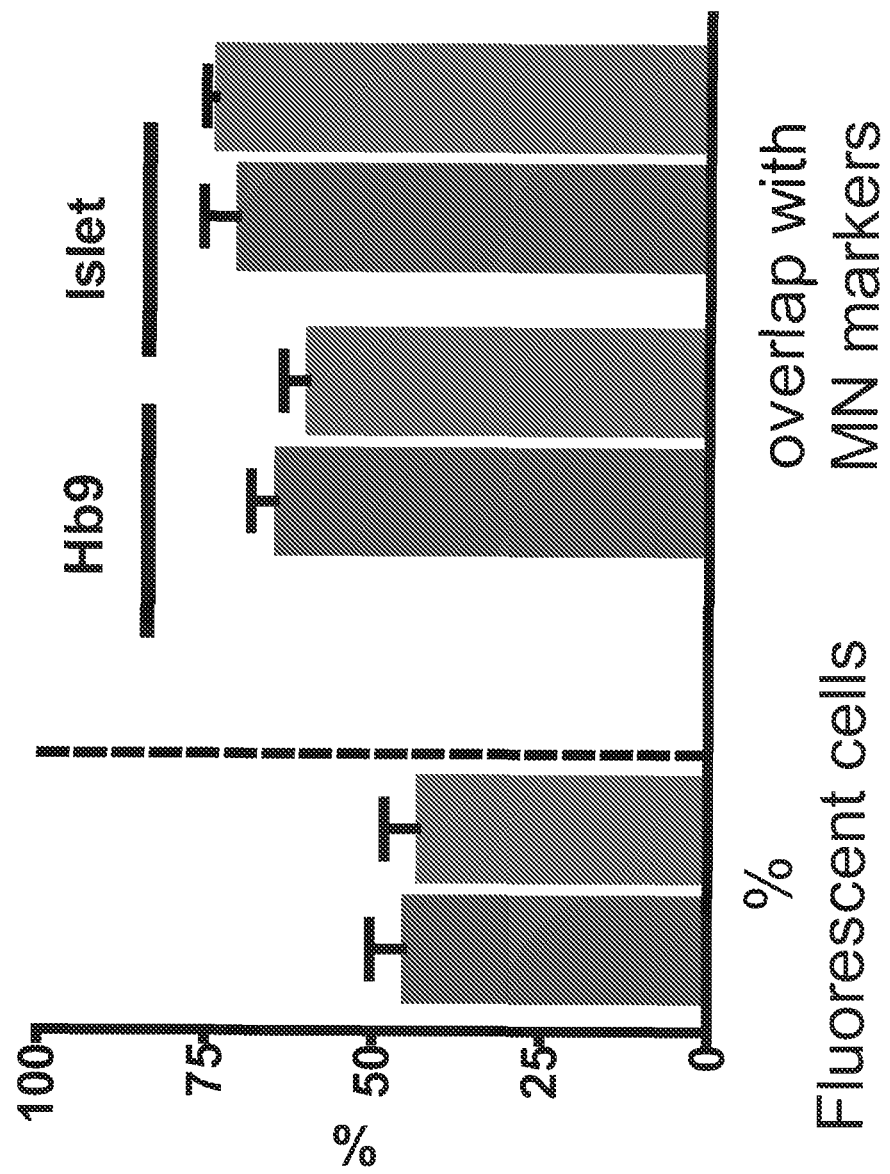

Mechanism Through which Stressors Trigger Preferential Degeneration of ALS Mouse Motor Neurons Not wishing to be bound to a particular theory, but based on the data and on the literature, the inventors hypothesize that CPA and thapsigargin induce the death of motor neurons through a set of pathways involving ER stress, decreased calcium buffering, calpains and caspases-12, 9 and 3 (FIG. 5). These are classical effectors of $Ca^{++}$ imbalance and have already been reported in motor neurons induced to express ALS-linked mutant forms of VAPB (Langou et al., 2010).

Two critical questions will be answered (a) at what level does mutant SOD1 sensitize motor neurons to CPA, and (b) what does this tell us about the functional state of motor neurons at this presymptomatic stage? For each of the key steps we will use a combination of techniques, focusing on those that show a difference between WT and G93A neurons and seeking thereby to locate the point in the pathway at which mutant SOD1 begins to affect the outcome as follows:

ER Stress:

To determine whether CPA induces ER stress we will use quantitative immunofluorescence to monitor the phosphorylation status of IRE1 and EIF2α, two widely used markers of ER stress (Saxena and Caroni, 2011). To ascertain whether or not ER stress is alone sufficient to trigger ALS-selective cell death, we will evaluate tunicamycin, which does not affect ER calcium transport, in the 2-color assay. A negative result might suggest that the selective effect of CPA is primarily $Ca^{++}$-dependent. In a complementary set of experiments we will ask whether ER-stress is necessary for CPA mediated toxicity to ALS motor neurons. Salubrinal, which inhibits ER stress by blocking phosphorylation of EIF2a, is protective in $SOD1^{G93A}$ mice in vivo (Saxena et al., 2009). We expected that it will correct the survival deficit of G93A neurons in vitro, thus providing another correlation between our assay and the in vivo setting.

$Ca^{++}$ Handling:

To first confirm that excess $Ca^{++}$ contributes to CPA-triggered death, we will incubate ES-MNs with the membrane-permeable $Ca^{++}$ chelator BAPTA/AM before treatment. To determine whether increased cytoplasmic $Ca^{++}$ is alone sufficient to generate ALS-selective cell death, we will treat ES-MNs of both genotypes with caffeine, which by activating ryanodine receptors releases $Ca^{++}$ from the ER. We will use Fura-2 imaging to ascertain whether the degree of $Ca^{++}$ release in each line is similar. If caffeine triggers death of both G93A and WT motor neurons, it will suggest that $Ca^{++}$ signaling is involved in CPA-triggered death but is not a determinant of selective vulnerability. If it confers on WT motor neurons the same sensitivity as G93A neurons, this will be a strong indicator that the enhanced $Ca^{++}$ release we observe from ER (FIG. 2) is a site of mSOD1-dependent vulnerability.

To determine whether $Ca^{++}$ from the ER is the relevant source, we will block release from the ER by inhibiting the ryanodine receptor (RyR). Cultures will be pretreated for 30 min with 30 μM dantrolene (or vehicle) and dantrolene will be present while cells are treated with CPA or other stressors.

We will pursue our studies to image $Ca^{++}$ handling in ES-MNs and will extend them to primary motor neurons isolated from the same SOD1 mice, since these have been shown to exhibit altered excitability in vitro (Quinlan et al., 2011). We will first attempt to confirm our observation of a greater $Ca^{++}$ accumulation in the cytoplasm of G93A cells following prolonged CPA application. This may reflect differences in ER release properties, which may be revealed by the above experiments with caffeine. Alternatively, differences in $Ca^{++}$ buffering by mitochondria may be detected by: 1) measuring the release triggered by the mitochondrial uncoupler FCCP; 2) measuring mitochondrial $Ca^{++}$ content using the Rhod-2 $Ca^{++}$ dye, which preferentially labels mitochondria; and 3) using a genetically-encoded sensor such as mt Pericam. Lastly, differences in the $Ca^{++}$-release-activated $Ca^{++}$ current (ICRAC) generated by store-operated channels (SOCs) in the plasma membrane may affect both peak size and recovery kinetics. We will use SOCE inhibitors ML-9 and 2-APB to determine their contribution (Gruszczynska-Biegala et al., 2011). It is of interest that blockade of SOCEs can lead to increases in neuronal excitability (Gemes et al., 2011).

Caspase-12:

Caspase-12 is an ER-associated member of the caspase family that is activated by $Ca^{++}$ release following ER stress (Nakagawa and Yuan, 2000), and of which only a truncated form is expressed in humans of non-African descent. Mouse caspase-12 knockout neurons, or WT neurons exposed to casp12 antisense oligonucleotides, are resistant to apoptosis induced by Aβ (Nakagawa et al., 2000). We will use the cell-permeant inhibitor peptide z-ATAD-fmk as a measure of caspase-12 involvement and quantitative immunohistochemistry to measure caspase-12 levels in the ER of WT and G93A cells.

Calpains:

Calpains are activated by increased $Ca^{++}$ and are known to play a role in neuronal death (Bevers and Neumar, 2008). We will use the pan-calpain inhibitor MDL-28170 to test their involvement.

Example 8

Preferential Vulnerability of Human iPS-MNs Derived from ALS Patients

The data set forth above demonstrate the feasibility of purifying iPS-MNs using a motor neuron-specific Hb9::RFP lentiviral vector and performing survival assays following FACS purification (FIG. 3). We aim to test the ability of the lead compounds from the mouse screen—CPA, thapsigargin, capsaicin, DH97 and 2,3-DCPE—on a panel of iPS lines from ALS patients and controls, which we have demonstrated to have robust and comparable properties for generation of motor neurons in vitro (Boulting et al., 2011). The experiments will first be performed on one ALS and one control iPS line and then extended to the full collection.

Method for Generation of Purified iPS-MNs.

Embryoid bodies containing differentiated motor neurons are dissociated at day 21-22 of differentiation and plated at $10^6$ cells per well in a 12-well plate (Boulting et al., 2011). Following infection with lentiviral supernatants, cells recover for a further 7-8 days to allow expression of virus. FACS sorting is performed on a BD FACS ARIA with low sheath pressure and a 100 μM nozzle size. The typical yield is about 15,000 motor neurons per 12-well and production is scaleable.

Survival and Outgrowth Assays.

To assay survival and neurite outgrowth in human iPS-MNs, we will initially use a 96-well plate culture system coupled with the same culture conditions that allowed us to develop robust assays for hES-MNs. FACS-sorted iPS-MNs will be seeded at 1,000 cells/well in culture media in the presence or absence of a cocktail of neurotrophic factors. At 1, 2, 4 and 7 days after seeding, motor neuron numbers in the whole well will be automatically quantified by their intrinsic fluorescence or AM-calcein staining using the Plate Runner imager (FIG. 3C) and MetaMorph software.

Given our success with survival assays from FACS-sorted human ES-MNs, we do not anticipate major problems in establishing similarly robust assays with iPS-MNs. One issue for the gene expression studies below may be the relatively low yield of motor neurons from the viral-infected cultures. Therefore, we will also prepare stable transfectants of a selected set of iPS lines with Hb9::GFP/RFP transgenes. These will allow us to prepare iPS-MNs as demonstrated for ES-MNs in FIG. 3.

Example 9

Effects of Overexpression or Knockdown of Candidate Genes and SERCA on iPS-MN Survival and Axon Growth Using initially a focused subset of 2 control and 2 ALS lines, we will measure the effects of overexpression or knockdown of each candidate gene on survival and axonal growth of control and ALS iPS-MNs. iPS-MNs will be seeded in 96-well dishes in the presence of neurotrophic factors, and one day later will be infected with viral vectors. Survival and growth will be monitored daily using the Plate Runner (FIGS. 3C-D). We will quantify the degree to which each candidate modifier induces degeneration as a function of time in culture and level of overexpression, and will compare effects on ALS and control iPS cells. To detect a role in sensitizing motor neurons, we will test the effects of misexpression in the presence of sublethal concentrations of the CPA, thapsigargin, capsaicin, DH97 and 2,3-DCPE. Results using single genes that give particularly striking results will be extended to the larger group of ALS and control cells. To provide a first characterization of the degenerative mechanism triggered by each modifier, we will perform the same experiments in the presence of two classes of inhibitor: (a) specific inhibitors of pathways known to be triggered by these stressors; and (b) specific inhibitors of pathways known to cause death of motor neurons in other systems, such as the Fas/NO pathway (Raoul et al., 2002).

Overexpression of any protein at excessive levels is liable to induce motor neuron degeneration, therefore it will be important to exclude artifacts. We will do this in three ways: (a) by ensuring that death triggered by viral infection is always <75% in the conditions studied; (b) by restricting levels of overexpression at the protein level to 2× that observed in the control or ALS iPS-MNs, whichever is higher; (c) by excluding data that suggest that the modifier is inducing necrotic rather than apoptotic cell death.

Example 10

Effects of Candidate Genes and SERCA on iPS-MN Excitability

We will test the effects of each gene on $Ca^{++}$ handling and excitability, and analyze the channels involved. Recording of membrane action potential firing properties, including threshold, time to first action potential, and repetitive firing properties, will be used as an initial screen for alterations in channel function following overexpression or knockdown of candidate genes. The outcome of this screen will direct the more detailed recording of membrane channel properties. For example, knockdown of DPP6 altered firing properties due to changes in sodium current, A current and leak channels (Nadin and Pfaffinger, 2010) and we will therefore study the A current and other channels in iPS-MNs. Disease modifiers may not only enhance excitability and thus $Ca^{++}$ entry, but also alter $Ca^{++}$ metabolism. For example, since it controls membrane $Ca^{++}$ pumps, CD44 may influence the ability of iPS-MNs to recover from a $Ca^{++}$ challenge.

Therefore, we will use $Ca^{++}$ imaging to investigate the impact of disease modifiers on $Ca^{++}$ entry and on recovery from a $Ca^{++}$ challenge. Using the approach illustrated in FIG. 2, we will use brief, 2-second applications of $Ca^{++}$ and kainate to depolarize iPS-MNs. In infected cells and mock-infected controls, peak responses will be compared as well as the time course of recovery from the depolarizing challenges. Changes in peak responses should reflect possible changes in $Ca^{++}$ entry and metabolism while changes in recovery time course should reflect primarily $Ca^{++}$ metabolism.

Example 11

Effects of SERCA Overexpression in mSOD1 Mice

Our data suggest that basal SERCA levels may be lower in ALS motor neurons than controls, and that SERCA inhibition can lead to ALS-selective motor neuron degeneration. Overexpression of SERCA pumps may therefore correct the basal deficit and make motor neurons more resistant to this and other stresses that tend to increase cytoplasmic $Ca^{++}$ levels. Encouragingly, AAV-based gene therapy to deliver SERCA2a has already shown promising results in human patients. In the CUPID trial using i.v. administration of AAV1::SERCA2a, the frequency of cardiovascular events was monitored over a 12-month period, with a significant decrease of cardiovascular hospitalization in the patients who received the highest of the three doses of vector administered (Jessup et al., 2011). And in an animal model of muscular dystrophy, AAV9::SERCA2a dramatically attenuated dystrophic disease in the injected gastrocnemius, showing 8-fold less central nucleation and preserved cellular architecture with little signs of necrosis (Goonasekera et al., 2011). We will therefore administer the AAV-Serca2a or another isoform of SERCA, such as SERCA2b4, to neonatal $SOD1^{G93A}$ mice by single injections at three distinct sites to compare efficacy: i.c.v., i.v. through facial vein, and i.m. into the TA muscle. We expect each approach to infect motor neurons efficiently (Foust et al., 2009). AAV9-GFP will be used as a control. We will monitor denervation of TA muscle at P50 as the primary endpoint, because that should be affected by all routes tested, and our power calculations from the MMP-9 experiments show that 4 animals are sufficient to detect significant effects. We will subsequently extend the study using the most effective route of administration to evaluate effects on muscle strength by CMAP, functional readouts such as swim test and rotarod, pathological parameters including motor neuron survival and axon counts in peripheral nerve and lifespan. For these more complete analyses, it will be necessary to treat 12 ALS mice per condition to obtain robust data (Mead et al., 2011).

Example 12

Figure 9:
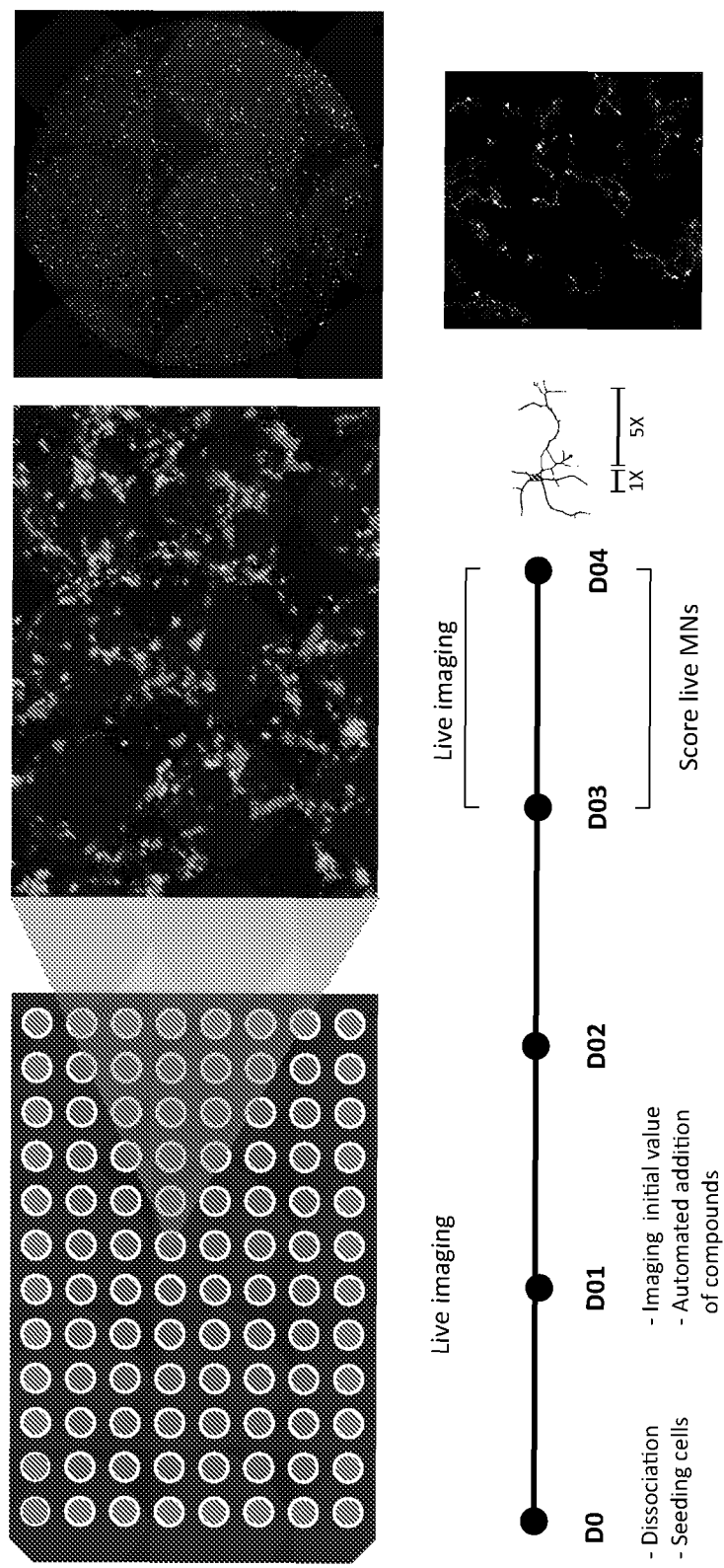
FIG. 9 shows a screening platform and design according to the present invention. GFP+ and RFP+ motor neurons were seeded in 96-well plates at equal proportions and imaged using a whole-well imaging platform (Plate Runner HD, Trophos, Marseilles, France). Live cells were scored with an automated image software (Metamorph, Molecular Devices, LLC, Sunnyvale, Calif.) using a neurite outgrowth criterion of five times the cell body diameter. Compounds from a small molecule library (Trophos) were loaded using automated liquid handling, and motor neuron survival was scored at 48 and 72 hours after exposure to stressors.

A Small Molecule Screen for Drugs Reversing Stressor-induced Generation of ALS Motor Neurons Mouse embryonic stem cells (ES) expressing human wild type (WT) or mutated (G93A) superoxide dismutase 1 (SOD1) in combination with RFP or GFP controlled by the motor neuron specific Hb9 reporter, will be differentiated into motor neurons using an established protocol (Wichterle et al. 2002). RFP expressing WT motor neurons will be mixed with GFP expressing mutant motor neurons, and seeded at a density of approximately 600 motor neurons of each genotype per well in 96-well imaging plates (FIG. 9). The outer rows and columns of each plate will be filled with water to prevent evaporation, thus leaving 60 wells/plates for seeding motor neurons. Cells will be seeded in a medium supplemented with 500 pg/mL glial derived neurotrophic factor (GDNF) and cyclic AMP elevating compounds (forskolin 10 µM and IBMX 100 µM). 10-15 plates will be prepared for each differentiation, which equals screening of 480-720 compounds per week in single replicates.

Figure 10:
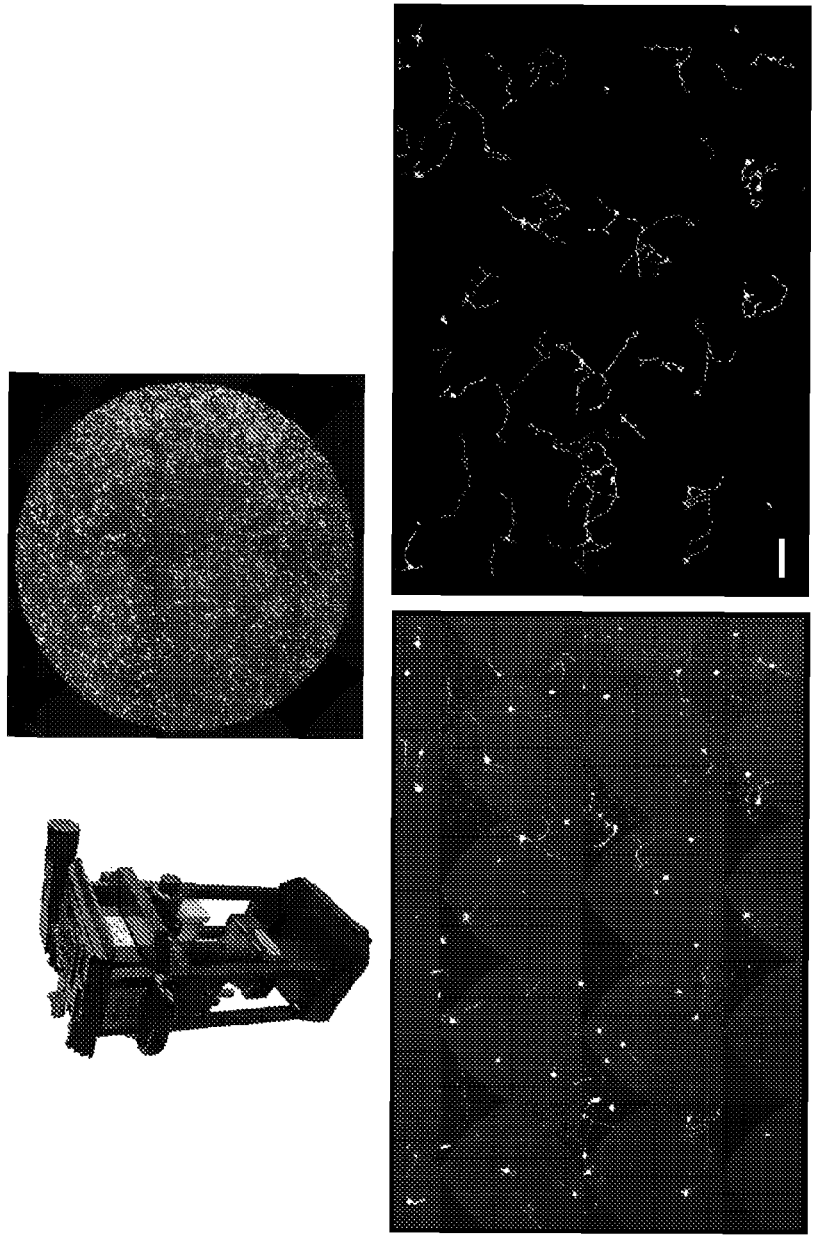
FIG. 10 shows that whole-well imaging combined with metamorph analysis ensures rigorous quantification of surviving motor neurons.
Figure 11:
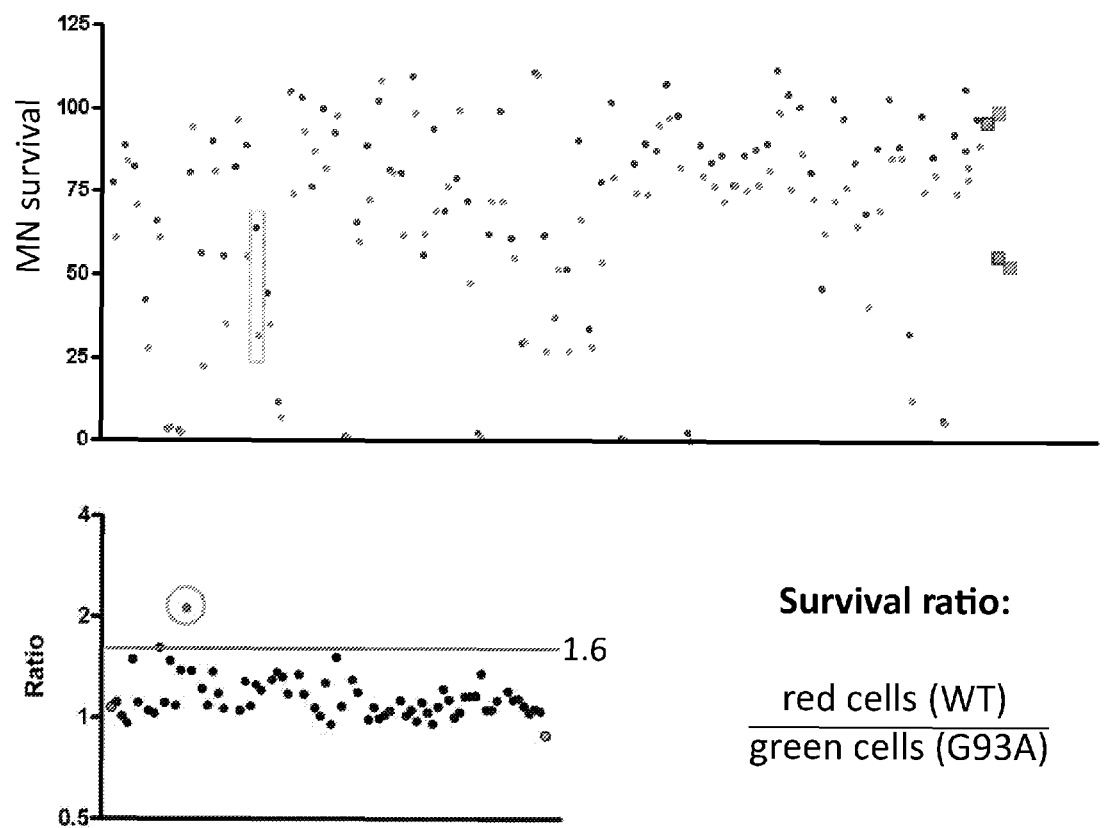
FIG. 11 shows the results of a pilot screen according to the present invention. Upper panel shows individual data points, in which dark gray points indicates WT survival and light gray points indicates ALS/G93A survival. Individual wells are displayed in the same vertical plane, e.g. see highlighted hit well in the upper panel. A survival ratio was calculated by dividing surviving % red cells with green cells for each well (lower left panel). Compounds eliciting ratios greater than 1.6 were considered hits (highlighted in lower left panel).

The plates will be imaged at 20 hours post plating using either the Trophos Plate Runner or the IN Cell Analyzer, to score initial motor neuron numbers. Automated and unbiased image analysis will be carried out using the Metamorph image software (FIG. 10).

Screen for Compounds Reversing CPA-mediated Toxicity

Figure 12:
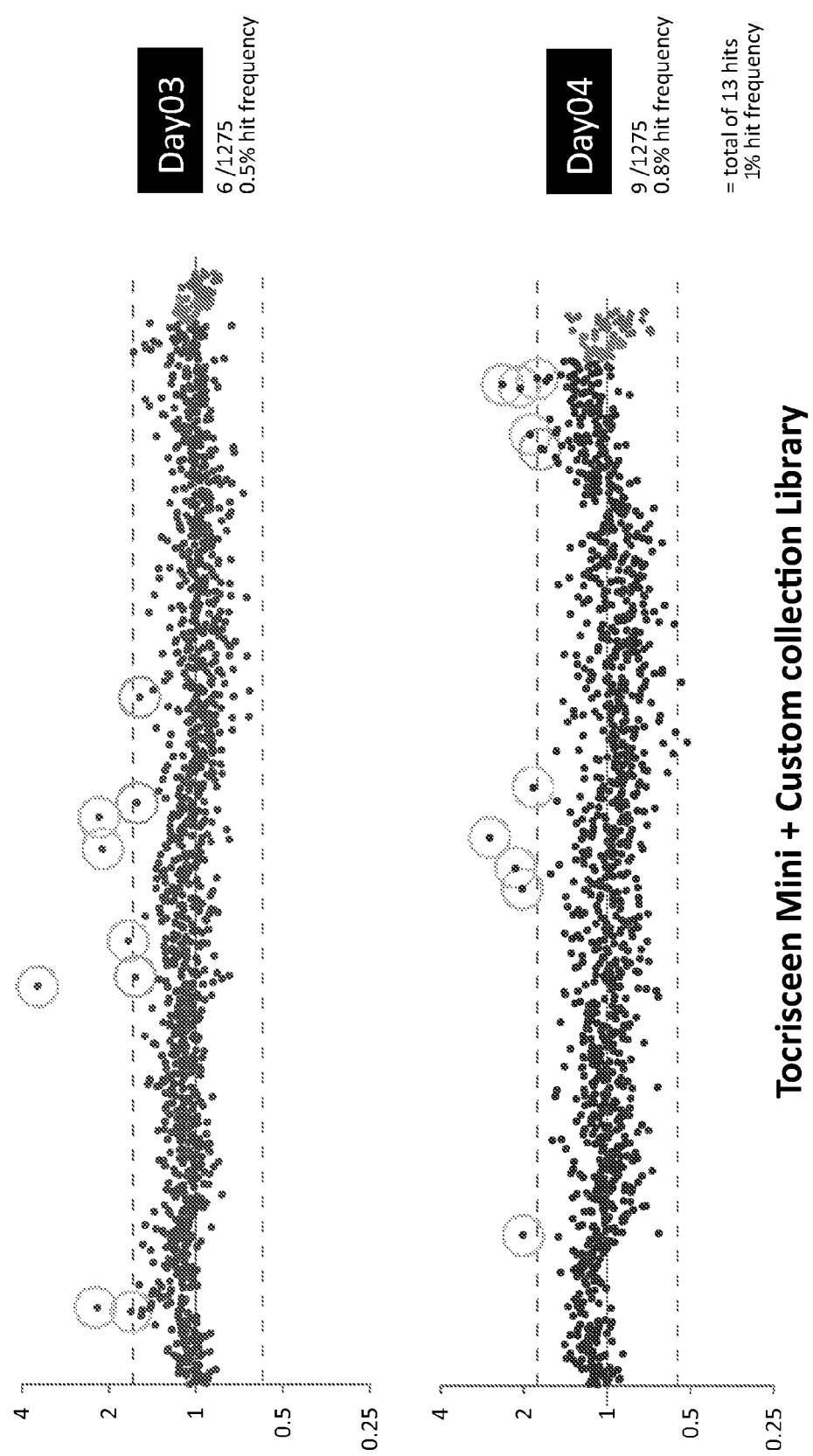
FIG. 12 shows the results of a primary screen according to the present invention. 1275 biologically active small molecules were screened for selective toxicity in ALS/G93A motor neurons.
Figure 13:
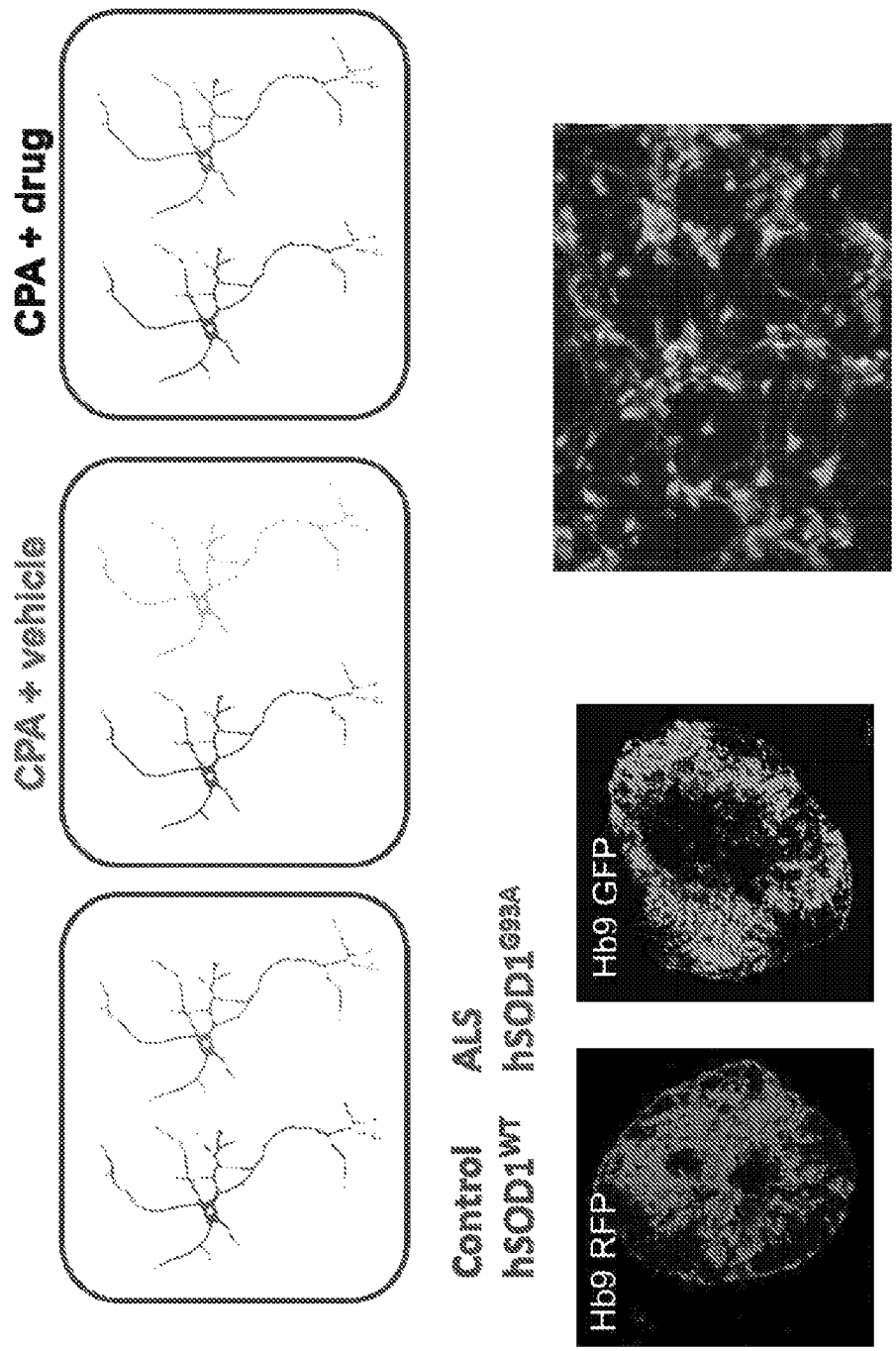
FIG. 13 shows the outline of the two-color screen for drugs interfering with CPA toxicity.

A library of small molecule compounds (Tocriscreen Mini & Custom collection, 1275 compounds, or other collections of novel compounds) will be added at a concentration of 10 µM using automated liquid handling. The compounds will be added to the wells following the 20 hour imaging time point. 6 wells per plate will be preincubated with a vehicle (negative control) and 6 wells will be preincubated with allosteric SERCA agonists, (Celladon Corp.) to serve as positive controls. The plates will be subsequently returned to recover in the incubator. After 60 minutes of preincubation with the compounds, CPA will be added to all wells at a concentration of 7.5 µM. This concentration normally results in approximately 40-50% reduction in WT motor neurons numbers after 48 hours and a survival ratio (red WT cells/green mutant cells) of 1.6-1.75 (FIG. 12). Compounds altering this ratio to 1.2 or lower, or increasing overall motor neuron survival, will be selected for validation and further characterization.

Human ALS Neurons Treated with CPA

To extend the translational impact of this project, we will screen for compounds neuroprotective to human ALS motor neurons. We will perform a drug screen analogous to the one described above for mouse cells, but adapted to a single color human cell system. Two human ES cell lines will be utilized: a control cell line carrying HB9-GFP transgene and an ALS line in which an A4V mutation has been introduced into the SOD1 gene using the TALENS system. ALS and control ES cells will be differentiated into motor neurons using an accelerated 21-day protocol (Amoroso et al., manuscript in preparation) or another protocol as set forth above. This 21-day differentiation protocol is well-characterized and robust, and can be expected to yield 20-30% GFP-positive cells. Control and SOD1-A4V mutant cells will be dissociated and seeded at 2000 cells/well in separate 96-well plates. As above, the outer wells of the plates will filled with water and excluded from the screen, such that 60 functional wells will be assayed per plate and each plate will contain 6 positive control wells (pretreated with SERCA agonists, Celladon Corp. before addition of CPA) and six negative cells (pretreated with vehicle prior to CPA treatment). Compounds will be added to motor neurons 60 minutes later. Motor neurons will be imaged immediately prior to the addition of the compounds using the Trophos Plate Runner or the IN Cell Analyzer to obtain initial cell counts, and then imaged again 72 and 120 hours later to assess neurite outgrowth and survival. All compounds will be tested at an initial concentration of 10 µM.

To further validate both the neuroprotective hits identified in human motor neurons, we will screen induced pluripotent stem (iPS) cell-derived motor neurons from ALS and control patients (Dimos et al. 2008) using the procedures set forth above.

Extension to Other Stressors Identified by 2-color Screens on Either Mouse or Human ES-MNs The ALS drug screen will be extended to other toxic compounds that were identified in the initial stressor screen (FIG. 12). Furthermore, new stressors that might act more selectively on human ALS motor neurons will be identified.

Example 13

The Screen for Drugs Reversing Stressor-induced Generation of ALS Motor Neurons is Validated Dissociated ESC-derived motor neurons expressing SOD1-G93A transgene were plated onto poly-ornithine and laminin coated substrates and allowed to recover for 24 hours. Tested compounds were added to the culture 1.5 hours prior to the treatment with 7.5 micromolar cyclopiazonic acid. Survival was scored after 24, 48 and 72 hours using a Plate Runner imaging platform. Automated image analysis and motor neuron quantification was performed using the Metamorph software.

Figure 14:
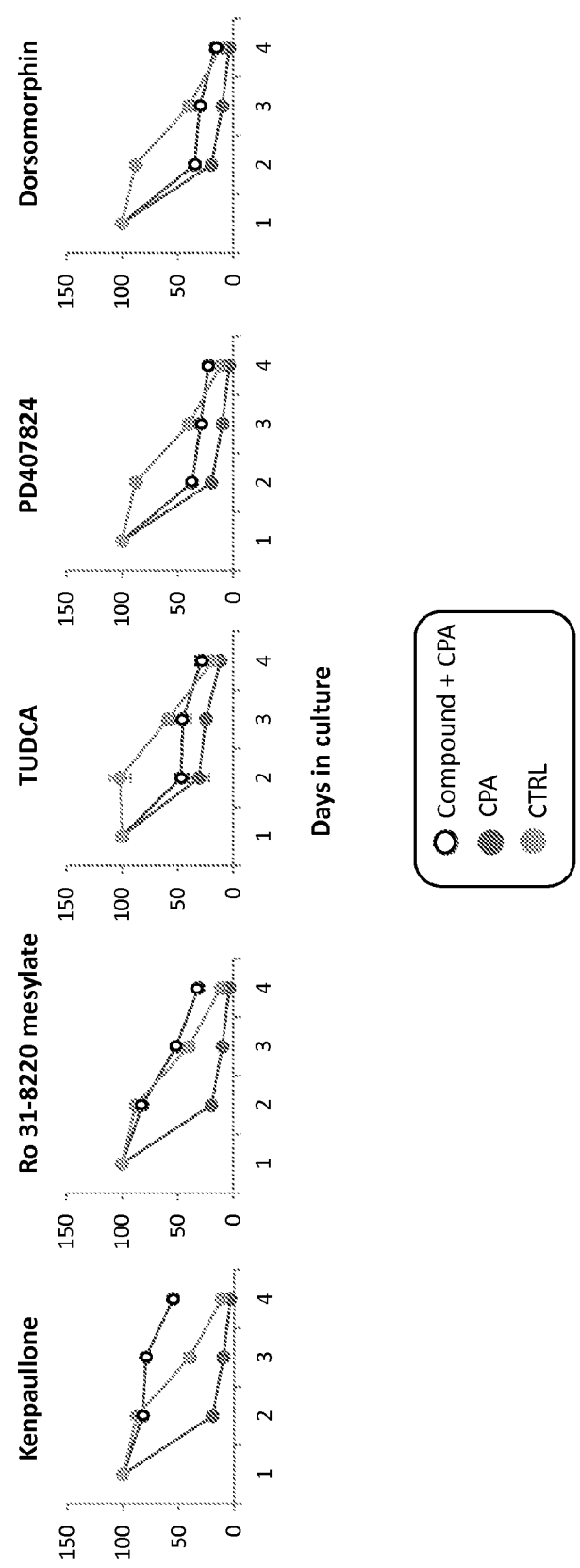
FIGS. 14A and 14B show five representative compounds identified using the methods of the present invention that have beneficial effects on motor neuron survival.

Five examples of compounds that were identified as having beneficial effect on motor neuron survival are shown in FIG. 14.

DOCUMENTS

Alvarez, J. L., Petzhold, D., Pankonien, I., Behlke, J., Kouno, M., Vassort, G., Morano, I., Haase, H., 2010. Ahnak1 modulates L-type Ca(2+) channel inactivation of rodent cardiomyocytes. Pflugers Arch 460, 719-730.

Batulan, Z., Taylor, D. M., Aarons, R. J., Minotti, S., Doroudchi, M. M., Nalbantoglu, J., Durham, H. D., 2006. Induction of multiple heat shock proteins and neuroprotection in a primary culture model of familial amyotrophic lateral sclerosis. Neurobiol Dis 24, 213-225.

Beltran-Parrazal, L., Fernandez-Ruiz, J., Toledo, R., Manzo, J., Morgado-Valle, C., 2012. Inhibition of endoplasmic reticulum Ca(2+) ATPase in preBötzinger complex of neonatal rat does not affect respiratory rhythm generation. Neuroscience 224C, 116-124.

Bevers, M. B., Neumar, R. W., 2008. Mechanistic role of calpains in postischemic neurodegeneration. J Cereb Blood Flow Metab 28, 655-673.

Blauw, H. M., Al-Chalabi, A., Andersen, P. M., van Vught, P. W., Diekstra, F. P., van Es, M. A., Saris, C. G., Groen, E. J., van Rheenen, W., Koppers, M., Van't Slot, R., Strengman, E., Estrada, K., Rivadeneira, F., Hofman, A., Uitterlinden, A. G., Kiemeney, L. A., Vermeulen, S. H., Birve, A., Waibel, S., Meyer, T., Cronin, S., McLaughlin, R. L., Hardiman, O., Sapp, P. C., Tobin, M. D., Wain, L. V., Tomik, B., Slowik, A., Lemmens, R., Rujescu, D., Schulte, C., Gasser, T., Brown, R. H., Jr., Landers, J. E., Robberecht, W., Ludolph, A. C., Ophoff, R. A., Veldink, J. H., van den Berg, L. H., 2010. A large genome scan for rare CNVs in amyotrophic lateral sclerosis. Hum Mol Genet 19, 4091-4099.

Bosco, D. A., Morfini, G., Karabacak, N. M., Song, Y., Gros-Louis, F., Pasinelli, P., Goolsby, H., Fontaine, B. A., Lemay, N., McKenna-Yasek, D., Frosch, M. P., Agar, J. N., Julien, J. P., Brady, S. T., Brown, R. H., 2010. Wild-type and mutant SOD1 share an aberrant conformation and a common pathogenic pathway in ALS. Nat Neurosci 13, 1396-1403.

Boulting, G. L., Kiskinis, E., Croft, G. F., Amoroso, M. W., Oakley, D. H., Wainger, B. J., Williams, D. J., Kahler, D. J., Yamaki, M., Davidow, L., Rodolfa, C. T., Dimos, J. T., Mikkilineni, S., MacDermott, A. B., Woolf, C. J., Henderson, C. E., Wichterle, H., Eggan, K., 2011. A functionally characterized test set of human induced pluripotent stem cells. Nat Biotechnol 29, 279-286.

Brotherton, T. E., Li, Y., Glass, J. D., 2012. Cellular toxicity of mutant SOD1 protein is linked to an easily soluble, non-aggregated form in vitro. Neurobiol Dis 49C, 49-56.

Carlson, S. S., Valdez, G., Sanes, J. R., 2010. Presynaptic calcium channels and alpha3-integrins are complexed with synaptic cleft laminins, cytoskeletal elements and active zone components. J Neurochem 115, 654-666.

Chio, A., Schymick, J. C., Restagno, G., Scholz, S. W., Lombardo, F., et al., 2009. A two-stage genome-wide association study of sporadic amyotrophic lateral sclerosis. Hum Mol Genet 18, 1524-1532.

Cleveland, D. W., Rothstein, J. D., 2001. From Charcot to Lou Gehrig: deciphering selective motor neuron death in ALS. Nat Rev Neurosci 2, 806-819.

Damiano, M., Starkov, A. A., Petri, S., Kipiani, K., Kiaei, M., Mattiazzi, M., Flint Beal, M., Manfredi, G., 2006. Neural mitochondrial Ca2+ capacity impairment precedes the onset of motor symptoms in G93A Cu/Zn-superoxide dismutase mutant mice. J Neurochem 96, 1349-1361.

de Morree, A., Droog, M., Grand Moursel, L., Bisschop, I. J., Impagliazzo, A., Frants, R. R., Klooster, R., van der Maarel, S. M., 2011. Self-regulated alternative splicing at the AHNAK locus. FASEB J.

Dimos, J. T., Rodolfa, K. T., Niakan, K. K., Weisenthal, L. M., Mitsumoto, H., Chung, W., Croft, G. F., Saphier, G., Leibel, R., Goland, R., Wichterle, H., Henderson, C. E., Eggan, K., 2008. Induced pluripotent stem cells generated from patients with ALS can be differentiated into motor neurons. Science 321, 1218-1221.

Elden, A. C., Kim, H. J., Hart, M. P., Chen-Plotkin, A. S., Johnson, B. S., Fang, X., Armakola, M., Geser, F., Greene, R., Lu, M. M., Padmanabhan, A., Clay-Falcone, D., McCluskey, L., Elman, L., Juhr, D., Gruber, P. J., Rub, U., Auburger, G., Trojanowski, J. Q., Lee, V. M., Van Deerlin, V. M., Bonini, N. M., Gitler, A. D., 2010. Ataxin-2 intermediate-length polyglutamine expansions are associated with increased risk for ALS. Nature 466, 1069-1075.

Foust, K. D., Nurre, E., Montgomery, C. L., Hernandez, A., Chan, C. M., Kaspar, B. K., 2009. Intravascular AAV9 preferentially targets neonatal neurons and adult astrocytes. Nat Biotechnol 27, 59-65.

Gehman, L. T., Stoilov, P., Maguire, J., Damianov, A., Lin, C. H., Shiue, L., Ares, M., Jr., Mody, I., Black, D. L., 2011. The splicing regulator Rbfoxl (A2BP1) controls neuronal excitation in the mammalian brain. Nat Genet 43, 706-711.

Gemes, G., Bangaru, M. L., Wu, H. E., Tang, Q., Weihrauch, D., Koopmeiners, A. S., Cruikshank, J. M., Kwok, W. M., Hogan, Q. H., 2011. Store-operated Ca2+ entry in sensory neurons: functional role and the effect of painful nerve injury. J Neurosci 31, 3536-3549.

Ghosh, B., Li, Y., Thayer, S. A., 2011. Inhibition of the plasma membrane Ca2+ pump by CD44 receptor activation of tyrosine kinases increases the action potential afterhyperpolarization in sensory neurons. J Neurosci 31, 2361-2370.

Goonasekera, S. A., Lam, C. K., Millay, D. P., Sargent, M. A., Najjar, R. J., Kranias, E. G., Molkentin, J. D., 2011.

Mitigation of muscular dystrophy in mice by SERCA overexpression in skeletal muscle. J Clin Invest 121, 1044-1052.

Grosskreutz, J., Van Den Bosch, L., Keller, B. U., 2010. Calcium dysregulation in amyotrophic lateral sclerosis. Cell Calcium 47, 165-174.

Gruszczynska-Biegala, J., Pomorski, P., Wisniewska, M. B., Kuznicki, J., 2011. Differential roles for STIM1 and STIM2 in store-operated calcium entry in rat neurons. PLoS One 6, e19285.

Igoudjil, A., Magrané, J., Fischer, L. R., Kim, H. J., Hervias, I., Dumont, M., Cortez, C., Glass, J. D., Starkov, A. A., Manfredi, G., 2011. In vivo pathogenic role of mutant SOD1 localized in the mitochondrial intermembrane space. J Neurosci 31, 15826-15837.

Jessup, M., Greenberg, B., Mancini, D., Cappola, T., Pauly, D. F., Jaski, B., Yaroshinsky, A., Zsebo, K. M., Dittrich, H., Najjar, R. J., Investigators, C.U.b.P.A.o.G.T.i.C.D.C., 2011. Calcium Upregulation by Percutaneous Administration of Gene Therapy in Cardiac Disease (CUPID): a phase 2 trial of intracoronary gene therapy of sarcoplasmic reticulum Ca2+-ATPase in patients with advanced heart failure. Circulation 124, 304-313.

Langou, K., Moumen, A., Pellegrino, C., Aebischer, J., Medina, I., Aebischer, P., Raoul, C., 2010. AAV-mediated expression of wild-type and ALS-linked mutant VAPB selectively triggers death of motoneurons through a Ca2+-dependent ER-associated pathway. J Neurochem 114, 795-809.

Lobsiger, C. S., Boillee, S., Cleveland, D. W., 2007. Toxicity from different SOD1 mutants dysregulates the complement system and the neuronal regenerative response in ALS motor neurons. Proc Natl Acad Sci USA 104, 7319-7326.

Mead, R. J., Bennett, E. J., Kennerley, A. J., Sharp, P., Sunyach, C., Kasher, P., Berwick, J., Pettmann, B., Battaglia, G., Azzouz, M., Grierson, A., Shaw, P. J., 2011. Optimised and rapid pre-clinical screening in the SOD1 (G93A) transgenic mouse model of amyotrophic lateral sclerosis (ALS). PLoS One 6, e23244.

Nadin, B. M., Pfaffinger, P. J., 2010. Dipeptidyl peptidase-like protein 6 is required for normal electrophysiological properties of cerebellar granule cells. J Neurosci 30, 8551-8565.

Nakagawa, T., Yuan, J., 2000. Cross-talk between two cysteine protease families. Activation of caspase-12 by calpain in apoptosis. J Cell Biol 150, 887-894.

Nakagawa, T., Zhu, H., Morishima, N., Li, E., Xu, J., Yankner, B. A., Yuan, J., 2000. Caspase-12 mediates endoplasmic-reticulum-specific apoptosis and cytotoxicity by amyloid-beta. Nature 403, 98-103.

Perrin, F. E., Boisset, G., Lathuiliere, A., Kato, A. C., 2006. Cell death pathways differ in several mouse models with motoneurone disease: analysis of pure motoneurone populations at a presymptomatic age. J Neurochem 98, 1959-1972.

Quinlan, K. A., Schuster, J. E., Fu, R., Siddique, T., Heckman, C. J., 2011. Altered postnatal maturation of electrical properties in spinal motoneurons in a mouse model of amyotrophic lateral sclerosis. J Physiol 589, 2245-2260.

Rabin, S. J., Kim, J. M., Baughn, M., Libby, R. T., Kim, Y. J., Fan, Y., La Spada, A., Stone, B., Ravits, J., 2010. Sporadic ALS has compartment-specific aberrant exon splicing and altered cell-matrix adhesion biology. Hum Mol Genet 19, 313-328.

Raoul, C., Estevez, A. G., Nishimune, H., Cleveland, D. W., deLapeyriere, 0., Henderson, C. E., Haase, G., Pettmann, B., 2002. Motoneuron death triggered by a specific pathway downstream of Fas. potentiation by ALS-linked SOD1 mutations. Neuron 35, 1067-1083.

Saxena, S., Cabuy, E., Caroni, P., 2009. A role for motoneuron subtype-selective ER stress in disease manifestations of FALS mice. Nat Neurosci 12, 627-636.

Saxena, S., Caroni, P., 2011. Selective neuronal vulnerability in neurodegenerative diseases: from stressor thresholds to degeneration. Neuron 71, 35-48.

Staats, K. A., Van Rillaer, M., Scheveneels, W., Verbesselt, R., Van Damme, P., Robberecht, W., Van Den Bosch, L., 2012. Dantrolene is neuroprotective in vitro, but does not affect survival in SOD1(G93A) mice. Neuroscience 220, 26-31.

Sun, W., Maffie, J. K., Lin, L., Petralia, R. S., Rudy, B., Hoffman, D. A., 2011. DPP6 establishes the A-type K(+) current gradient critical for the regulation of dendritic excitability in CA1 hippocampal neurons. Neuron 71, 1102-1115.

Towne, C., Aebischer, P., 2009. Lentiviral and adeno-associated vector-based therapy for motor neuron disease through RNAi. Methods Mol Biol 555, 87-108.

Tradewell, M. L., Cooper, L. A., Minotti, S., Durham, H. D., 2011. Calcium dysregulation, mitochondrial pathology and protein aggregation in a culture model of amyotrophic lateral sclerosis: mechanistic relationship and differential sensitivity to intervention. Neurobiol Dis 42, 265-275.

Turner, B. J., Talbot, K., 2008. Transgenics, toxicity and therapeutics in rodent models of mutant SOD1-mediated familial ALS. Prog Neurobiol 85, 94-134.

Valdez, G., Tapia, J. C., Lichtman, J. W., Fox, M. A., Sanes, J. R., 2012. Shared resistance to aging and ALS in neuromuscular junctions of specific muscles. PLoS One 7, e34640.

Van Den Bosch, L., Verhoeven, K., De Smedt, H., Wuytack, F., Missiaen, L., Robberecht, W., 1999. Calcium handling proteins in isolated spinal motoneurons. Life Sci 65, 1597-1606.

Wang, J., Farr, G. W., Zeiss, C. J., Rodriguez-Gil, D. J., Wilson, J. H., Furtak, K., Rutkowski, D. T., Kaufman, R. J., Ruse, C. I., Yates, J. R., Perrin, S., Feany, M. B., Horwich, A. L., 2009. Progressive aggregation despite chaperone associations of a mutant SOD1-YFP in transgenic mice that develop ALS. Proc Natl Acad Sci USA 106, 1392-1397.

Yu, Q., Stamenkovic, I., 1999. Localization of matrix metalloproteinase 9 to the cell surface provides a mechanism for CD44-mediated tumor invasion. Genes Dev 13, 35-48.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for identifying a candidate agent comprising:
   (a) contacting a labeled wildtype neuron and a labeled mutant neuron with a chemical stressor which is effective to accelerate the degeneration of the labeled mutant neuron,
      wherein the mutant neuron comprises one or more mutations in the gene encoding superoxide dismutase 1 (SOD1), and
      wherein the chemical stressor is selected by mixed culture assay comprising equal proportions of wildtype and mutant neurons as having a wildtype-to-mutant survival ratio of greater than 1.6 after 48 hours;
(b) further contacting the labeled wildtype neurons and the labeled mutant neurons from step (a) with a candidate agent; and
(c) detecting the label of the wildtype neuron and the label of the mutant neuron to determine whether the candidate agent lowers a wildtype to mutant survival ratio or increases both wildtype and mutant neuron survival.

2. The method according to claim 1, wherein the wildtype or the mutant neuron is a motor neuron.

3. The method according to claim 2, wherein the wildtype or the mutant neuron is a mammalian neuron.

4. The method according to claim 3, wherein the wildtype or the mutant neuron is a mouse neuron.

5. The method according to claim 3, wherein the wildtype or the mutant neuron is a human neuron.

6. The method according to claim 1, wherein the wildtype or the mutant neuron is generated in vitro from embryonic stem cells.

7. The method according to claim 1, wherein the wildtype or the mutant neuron is an induced pluripotent stem (iPS) cell-derived motor neuron (iPS-MN).

8. The method according to claim 1, wherein the stressor is selected from the group consisting of an agonist of the TRPV2 receptor, a sarco(endo)-plasmic reticulum $Ca^{++}$-ATPase (SERCA) inhibitor, a MT2melatonin receptor inhibitor, and a Bcl-xL inhibitor.

9. The method according to claim 8, wherein the stressor is a SERCA inhibitor.

10. The method according to claim 9, wherein the SERCA inhibitor is selected from the group consisting of cyclopiazonic acid (CPA) and thapsigargin.

11. The method according to claim 1, wherein the mutant neuron contains a SOD1-G93A mutation.

12. The method according to claim 1, wherein the wildtype neuron and the mutant neuron are labeled differently.

* * * * *